(12) United States Patent
Aklog et al.

(10) Patent No.: US 11,141,186 B2
(45) Date of Patent: Oct. 12, 2021

(54) SYSTEMS AND METHODS FOR PERCUTANEOUS DIVISION OF FIBROUS STRUCTURES

(71) Applicant: PAVmed Inc., New York, NY (US)

(72) Inventors: Lishan Aklog, New York, NY (US); Brian J. deGuzman, Paradise Valley, AZ (US)

(73) Assignee: PAVmed Inc., New York, NY (US)

( * ) Notice: Subject to any disclaimer, the term of this patent is extended or adjusted under 35 U.S.C. 154(b) by 649 days.

(21) Appl. No.: 15/964,531

(22) Filed: Apr. 27, 2018

(65) Prior Publication Data

US 2018/0242995 A1 Aug. 30, 2018

Related U.S. Application Data

(62) Division of application No. 14/958,003, filed on Dec. 3, 2015, now Pat. No. 10,335,189.

(Continued)

(51) Int. Cl.
*A61B 18/12* (2006.01)
*A61B 17/3209* (2006.01)
(Continued)

(52) U.S. Cl.
CPC .. *A61B 17/3209* (2013.01); *A61B 17/320036* (2013.01); *A61B 17/320725* (2013.01);
(Continued)

(58) Field of Classification Search
CPC .... A61B 17/320016; A61B 17/320036; A61B 17/320725; A61B 17/3209;
(Continued)

(56) References Cited

U.S. PATENT DOCUMENTS 4,976,711 A 12/1990 Parins et al.
4,998,933 A 3/1991 Eggers et al.
(Continued)

FOREIGN PATENT DOCUMENTS

EP 0565796 10/1993
WO 1998/033445 8/1998

OTHER PUBLICATIONS

PCT International Search Report Issued in International Application No. PCT/US2015/063703 dated Feb. 5, 2016.

*Primary Examiner* — Daniel W Fowler
(74) *Attorney, Agent, or Firm* — Greenberg Traurig, LLP; Chinh H. Pham

(57) ABSTRACT

A device for dividing a fibrous structure comprising a catheter; an expandable member positioned near a distal end of the catheter and in fluid communication with a lumen of the catheter; and a cutting element situated on an outer surface of the expandable member. A method for dividing a fibrous structure comprising positioning, proximate the fibrous structure, an expandable member having a cutting element situated thereon; expanding the expandable member outwards to tension the fibrous structure across the cutting element; and activating the cutting element to weaken or cut the fibrous structure. A method for treating carpal tunnel syndrome comprising inserting a needle into the carpal tunnel; directing a guidewire to a position proximate the transverse carpal ligament; advancing, along the guidewire, a device having an expandable member and a cutting element; positioning the cutting element; tensioning the ligament across the cutting element; and weakening or cutting the ligament.

17 Claims, 27 Drawing Sheets

Related U.S. Application Data

(60) Provisional application No. 62/086,950, filed on Dec. 3, 2014.

(51) Int. Cl.
*A61B 17/32* (2006.01)
*A61B 17/3207* (2006.01)
*A61B 90/30* (2016.01)
*A61B 18/14* (2006.01)
*A61B 17/22* (2006.01)
*A61B 17/00* (2006.01)
*A61B 18/00* (2006.01)

(52) U.S. Cl.
CPC .......... *A61B 18/1492* (2013.01); *A61B 90/30* (2016.02); *A61B 17/320016* (2013.01); *A61B 2017/00039* (2013.01); *A61B 2017/00057* (2013.01); *A61B 2017/22061* (2013.01); *A61B 2017/320056* (2013.01); *A61B 2018/0022* (2013.01); *A61B 2018/00565* (2013.01); *A61B 2018/00601* (2013.01); *A61B 2018/00839* (2013.01); *A61B 2018/1412* (2013.01)

(58) Field of Classification Search
CPC ...... A61B 18/1492; A61B 2017/00057; A61B 2017/20061; A61B 2017/320056; A61B 2018/0022; A61B 2018/00565; A61B 2018/00601; A61B 2018/00839; A61B 2018/1412
See application file for complete search history.

(56) References Cited

U.S. PATENT DOCUMENTS

| | | |
|---|---|---|
| 5,100,425 A | 3/1992 | Fischell et al. |
| 5,196,024 A | 3/1993 | Barath |
| 5,209,799 A | 5/1993 | Vigil |
| 5,320,634 A | 6/1994 | Vigil et al. |
| 5,336,234 A | 8/1994 | Vigil et al. |
| 5,344,398 A | 9/1994 | Hara |
| 5,540,681 A | 7/1996 | Strul et al. |
| 5,547,469 A | 8/1996 | Rowland et al. |
| 5,573,533 A | 11/1996 | Strul |
| 5,616,149 A | 4/1997 | Barath |
| 5,628,746 A | 5/1997 | Clayman |
| RE35,523 E | 6/1997 | Berger |
| 5,697,944 A | 12/1997 | Lary |
| 5,713,913 A | 2/1998 | Lary et al. |
| 5,792,158 A | 8/1998 | Lary |
| 5,797,935 A | 8/1998 | Barath |
| 5,904,679 A | 5/1999 | Clayman |
| 5,908,433 A | 6/1999 | Eager et al. |
| 6,024,740 A | 2/2000 | Lesh et al. |
| 6,033,397 A | 3/2000 | Laufer et al. |
| 6,036,689 A | 3/2000 | Tu et al. |
| 6,036,713 A | 3/2000 | Kieturakis |
| 6,041,260 A | 3/2000 | Stern et al. |
| 6,080,102 A | 6/2000 | Konou et al. |
| 6,117,153 A | 9/2000 | Lary et al. |
| 6,165,187 A | 12/2000 | Reger |
| 6,190,355 B1 | 2/2001 | Hastings |
| 6,193,653 B1 | 2/2001 | Evans et al. |
| 6,214,024 B1 | 4/2001 | Houser |
| 6,231,572 B1 | 5/2001 | Hart et al. |
| 6,245,026 B1 | 6/2001 | Campbell et al. |
| 6,258,108 B1 | 7/2001 | Lary |
| 6,306,151 B1 | 10/2001 | Lary |
| 6,319,242 B1 | 11/2001 | Patterson et al. |
| 6,405,732 B1 | 6/2002 | Edwards et al. |
| 6,423,058 B2 | 7/2002 | Edwards et al. |
| 6,425,877 B1 | 7/2002 | Edwards |
| 6,440,128 B1 | 8/2002 | Edwards et al. |
| 6,443,927 B1 | 9/2002 | Rowland et al. |
| 6,464,697 B1 | 10/2002 | Edwards et al. |
| 6,488,679 B1 | 12/2002 | Swanson et al. |
| 6,500,186 B2 | 12/2002 | Lafontaine et al. |
| 6,562,062 B2 | 5/2003 | Jenusaitis et al. |
| 6,632,231 B2 | 10/2003 | Radisch |
| 6,673,066 B2 | 1/2004 | Werneth |
| 6,746,463 B1 | 6/2004 | Schwartz |
| 6,936,047 B2 | 8/2005 | Nasab et al. |
| 6,942,680 B2 | 9/2005 | Grayzel et al. |
| 6,951,566 B2 | 10/2005 | Lary |
| 6,971,395 B2 | 12/2005 | Edwards et al. |
| 7,008,438 B2 | 3/2006 | O'Brien |
| 7,011,670 B2 | 3/2006 | Radisch |
| 7,018,391 B2 | 3/2006 | Spitz et al. |
| 7,029,450 B2 | 4/2006 | Gellman |
| 7,029,483 B2 | 4/2006 | Schwartz |
| 7,070,576 B2 | 7/2006 | O'Brien et al. |
| 7,153,315 B2 | 12/2006 | Miller |
| 7,172,609 B2 | 2/2007 | Radisch |
| 7,186,237 B2 | 3/2007 | Meyer et al. |
| 7,270,673 B2 | 9/2007 | Yee et al. |
| 7,279,002 B2 | 10/2007 | Shaw et al. |
| 7,291,158 B2 | 11/2007 | Crow et al. |
| 7,303,572 B2 | 12/2007 | Melsheimer et al. |
| 7,338,463 B2 | 3/2008 | Vigil |
| 7,344,535 B2 | 3/2008 | Stern et al. |
| 7,396,358 B2 | 7/2008 | Appling et al. |
| 7,413,558 B2 | 8/2008 | Kelley et al. |
| 7,462,179 B2 | 12/2008 | Edwards et al. |
| 7,494,497 B2 | 2/2009 | Weber |
| 7,517,352 B2 | 4/2009 | Evans et al. |
| 7,530,979 B2 | 5/2009 | Ganz et al. |
| 7,611,482 B2 | 11/2009 | Naimark et al. |
| 7,632,288 B2 | 12/2009 | Wu |
| 7,641,633 B2 | 1/2010 | Laufer et al. |
| 7,648,500 B2 | 1/2010 | Edwards et al. |
| 7,658,744 B2 | 2/2010 | Jackson |
| 7,662,163 B2 | 2/2010 | Grayzel et al. |
| 7,691,116 B2 | 4/2010 | Goodin et al. |
| 7,736,375 B2 | 6/2010 | Crow |
| 7,753,907 B2 | 7/2010 | DiMatteo et al. |
| 7,754,047 B2 | 7/2010 | Kelley |
| 7,758,604 B2 | 7/2010 | Wu et al. |
| 7,771,447 B2 | 8/2010 | Kunis |
| 7,780,626 B2 | 8/2010 | Wu |
| 7,799,043 B2 | 9/2010 | O'Brien et al. |
| 7,879,053 B2 | 2/2011 | Trinidad |
| 7,887,557 B2 | 2/2011 | Kelley et al. |
| 7,901,402 B2 | 3/2011 | Jones et al. |
| 7,959,627 B2 | 6/2011 | Utley et al. |
| 7,976,557 B2 | 7/2011 | Kunis |
| 7,985,234 B2 | 7/2011 | Wang et al. |
| 7,993,358 B2 | 8/2011 | O'Brien |
| 8,034,066 B2 | 10/2011 | Goeken et al. |
| 8,038,691 B2 | 10/2011 | Bence et al. |
| 8,043,259 B2 | 10/2011 | Radisch, Jr. et al. |
| 8,043,311 B2 | 10/2011 | Radisch, Jr. et al. |
| 8,048,093 B2 | 11/2011 | Mapes et al. |
| 8,052,701 B1 | 11/2011 | Cox et al. |
| 8,052,703 B2 | 11/2011 | St. Martin et al. |
| 8,066,726 B2 | 11/2011 | Kelley |
| 8,109,951 B2 | 2/2012 | Maschke |
| 8,123,770 B2 | 2/2012 | Olsen et al. |
| 8,142,422 B2 | 3/2012 | Makower et al. |
| 8,202,285 B2 | 6/2012 | Goodin et al. |
| 8,361,096 B2 | 1/2013 | Bence et al. |
| 8,364,237 B2 | 1/2013 | Stone et al. |
| 8,377,055 B2 | 2/2013 | Jackson et al. |
| 8,377,083 B2 | 2/2013 | Mauch et al. |
| 8,401,667 B2 | 3/2013 | Gustus et al. |
| 8,412,318 B2 | 4/2013 | Edwards et al. |
| 8,439,908 B2 | 5/2013 | Utley et al. |
| 8,454,636 B2 | 6/2013 | Konstantino et al. |
| 8,454,637 B2 | 6/2013 | Aggerholm et al. |
| 8,491,615 B2 | 7/2013 | Manderfeld et al. |
| 8,496,653 B2 | 7/2013 | Steinke |
| 8,523,887 B2 | 9/2013 | Grayzel et al. |
| 8,568,416 B2 | 10/2013 | Schmitz et al. |
| 8,641,709 B2 | 2/2014 | Sauvageau et al. |

(56) References Cited

U.S. PATENT DOCUMENTS

| | | |
|---|---|---|
| 8,679,141 B2 | 3/2014 | Goodin et al. |
| 8,685,049 B2 | 4/2014 | Schur et al. |
| 8,690,903 B2 | 4/2014 | Bence et al. |
| 8,702,736 B2 | 4/2014 | Schur et al. |
| 8,721,636 B2 | 5/2014 | Vaska et al. |
| 8,740,846 B2 | 6/2014 | Edwards et al. |
| 8,740,896 B2 | 6/2014 | Zarins et al. |
| 8,774,922 B2 | 7/2014 | Zarins et al. |
| 8,818,514 B2 | 8/2014 | Demarais et al. |
| 8,855,778 B2 | 10/2014 | Rezai |
| 8,870,816 B2 | 10/2014 | Chambers et al. |
| 8,906,049 B2 | 12/2014 | Chambers |
| 8,920,414 B2 | 12/2014 | Stone et al. |
| 8,939,970 B2 | 1/2015 | Stone et al. |
| 8,945,168 B2 | 2/2015 | Davies et al. |
| 8,951,251 B2 | 2/2015 | Willard |
| 8,958,871 B2 | 2/2015 | Demarais et al. |
| 8,986,248 B2 | 3/2015 | Kunis |
| 9,017,343 B2 | 4/2015 | Bence et al. |
| 10,335,189 B2 | 7/2019 | Aklog et al. |
| 10,357,272 B2 | 7/2019 | Barnes et al. |
| 10,413,346 B2 | 9/2019 | Wallace |
| 10,864,055 B2 | 12/2020 | Barnes et al. |
| 2002/0082592 A1 | 6/2002 | Lary |
| 2003/0144683 A1 | 7/2003 | Sirhan et al. |
| 2004/0098014 A1 | 5/2004 | Flugelman et al. |
| 2005/0070888 A1 | 3/2005 | Dimatteo et al. |
| 2005/0177130 A1 | 8/2005 | Konstantino et al. |
| 2005/0240148 A1 | 10/2005 | Cheves et al. |
| 2006/0116700 A1 | 6/2006 | Crow |
| 2006/0178685 A1 | 8/2006 | Melsheimer |
| 2006/0184191 A1 | 8/2006 | O'Brien |
| 2006/0276782 A1 | 12/2006 | Gedebou |
| 2007/0198047 A1 | 8/2007 | Schon et al. |
| 2007/0213761 A1 | 9/2007 | Murphy et al. |
| 2008/0077164 A1 | 3/2008 | Murphy |
| 2008/0077165 A1 | 3/2008 | Murphy |
| 2008/0300610 A1 | 12/2008 | Chambers |
| 2009/0270892 A1 | 10/2009 | Arcenio et al. |
| 2010/0010521 A1 | 1/2010 | Kumus |
| 2010/0125266 A1 | 5/2010 | Deem et al. |
| 2010/0168611 A1 | 7/2010 | Hashimshony et al. |
| 2010/0241148 A1 | 9/2010 | Schon et al. |
| 2010/0274271 A1 | 10/2010 | Kelley |
| 2010/0286594 A1 | 11/2010 | Chambers |
| 2010/0312264 A1 | 12/2010 | O'Brien et al. |
| 2011/0119601 A1 | 5/2011 | Knothe et al. |
| 2011/0160756 A1 | 6/2011 | Aggerholm et al. |
| 2011/0301625 A1 | 12/2011 | Mauch et al. |
| 2011/0306996 A1 | 12/2011 | MCormack et al. |
| 2012/0022563 A1 | 1/2012 | Leffel |
| 2012/0191112 A1 | 7/2012 | Zamboni |
| 2012/0215251 A1 | 8/2012 | Burton et al. |
| 2012/0316589 A1 | 12/2012 | Schaeffer |
| 2013/0018396 A1 | 1/2013 | Gunderson et al. |
| 2013/0023912 A1 | 1/2013 | Brown et al. |
| 2013/0053851 A1 | 2/2013 | Schmitz et al. |
| 2013/0060127 A1 | 3/2013 | Burton et al. |
| 2013/0066257 A1 | 3/2013 | Folan et al. |
| 2013/0066346 A1 | 3/2013 | Pigott |
| 2013/0072815 A1 | 3/2013 | Hashimshony et al. |
| 2013/0131709 A1 | 5/2013 | Davies et al. |
| 2013/0131770 A1 | 5/2013 | Rezai |
| 2013/0165916 A1 | 6/2013 | Mathur et al. |
| 2013/0165962 A1 | 6/2013 | Porshinsky et al. |
| 2014/0088624 A1 | 3/2014 | Burton et al. |
| 2014/0128895 A1 | 5/2014 | Bence et al. |
| 2014/0155920 A1 | 6/2014 | Schur et al. |
| 2014/0163593 A1 | 6/2014 | Schur et al. |
| 2014/0277002 A1 | 9/2014 | Grace |
| 2014/0277059 A1 | 9/2014 | Lam et al. |
| 2014/0296888 A1 | 10/2014 | Schur et al. |
| 2014/0303617 A1 | 10/2014 | Shimada |
| 2021/0059759 A1 | 3/2021 | Asirvatham et al. |
| 2021/0069465 A1 | 3/2021 | Daniels et al. |

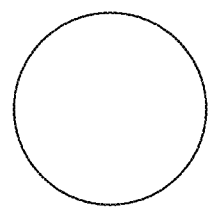
*FIG. 4B₁*
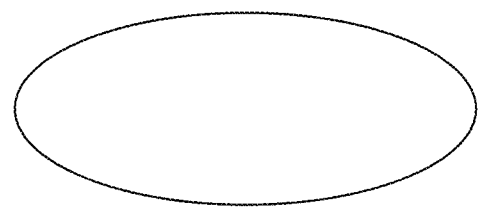
*FIG. 4B₂*
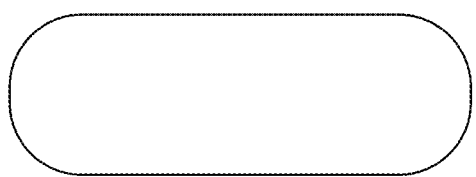
*FIG. 4B₃*
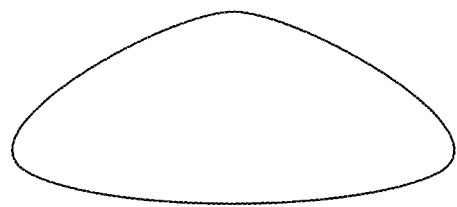
*FIG. 4B₄*
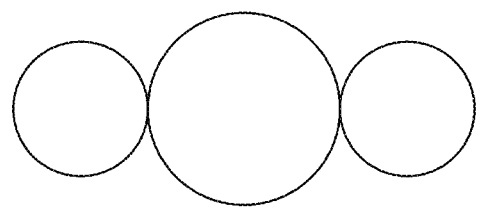
*FIG. 4B₅*

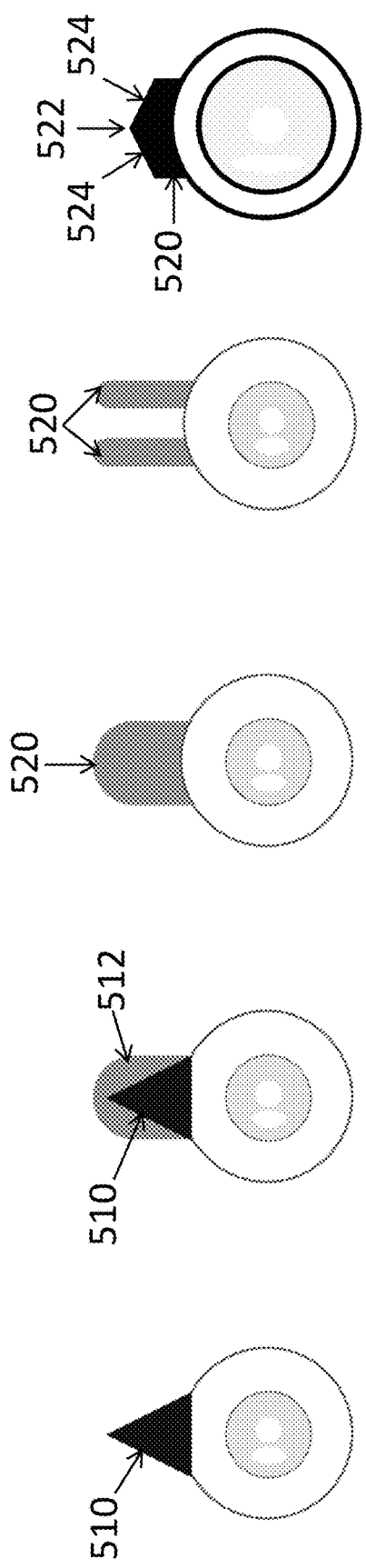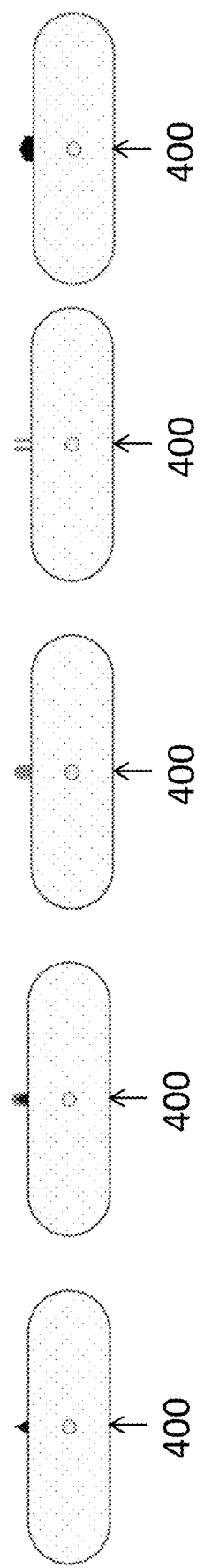
FIG. 5A  FIG. 5B  FIG. 6A  FIG. 6B  FIG. 6C

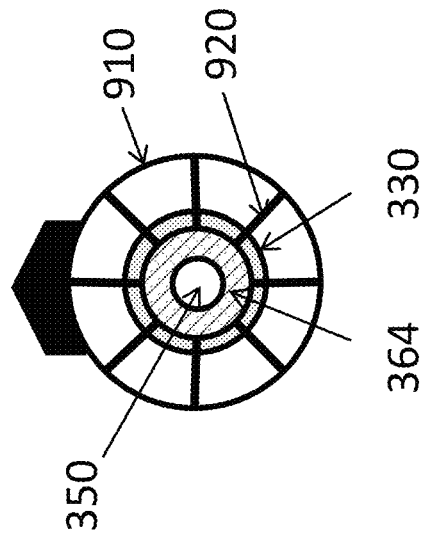
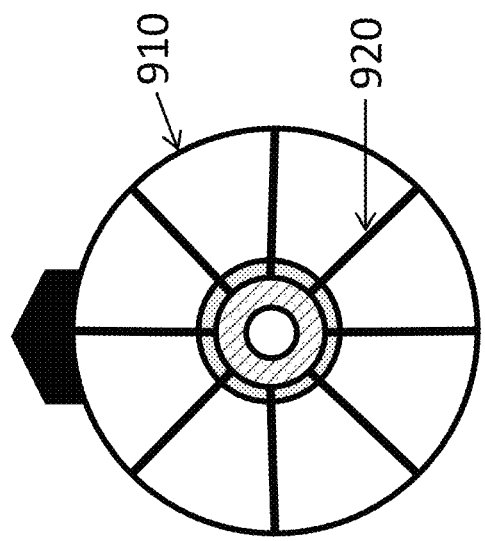
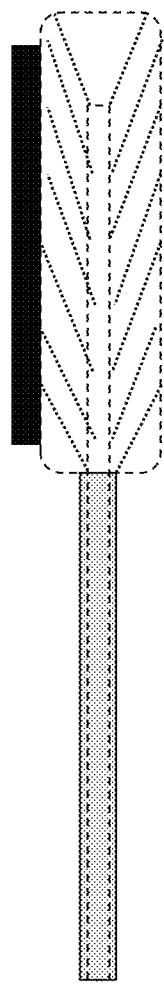
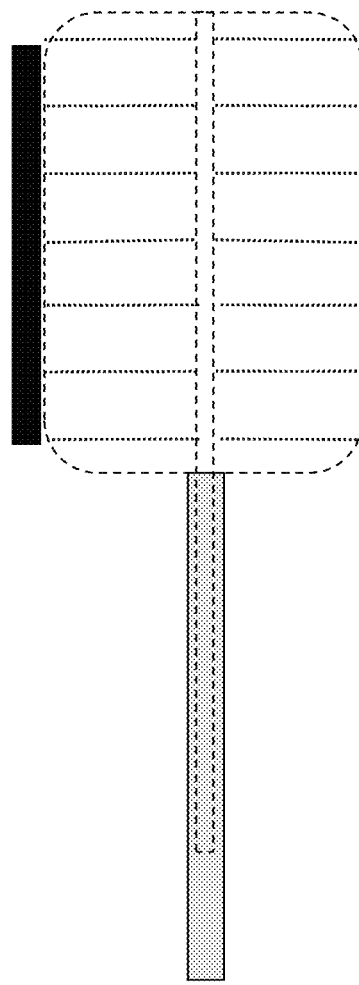
FIG. 10A
FIG. 10B

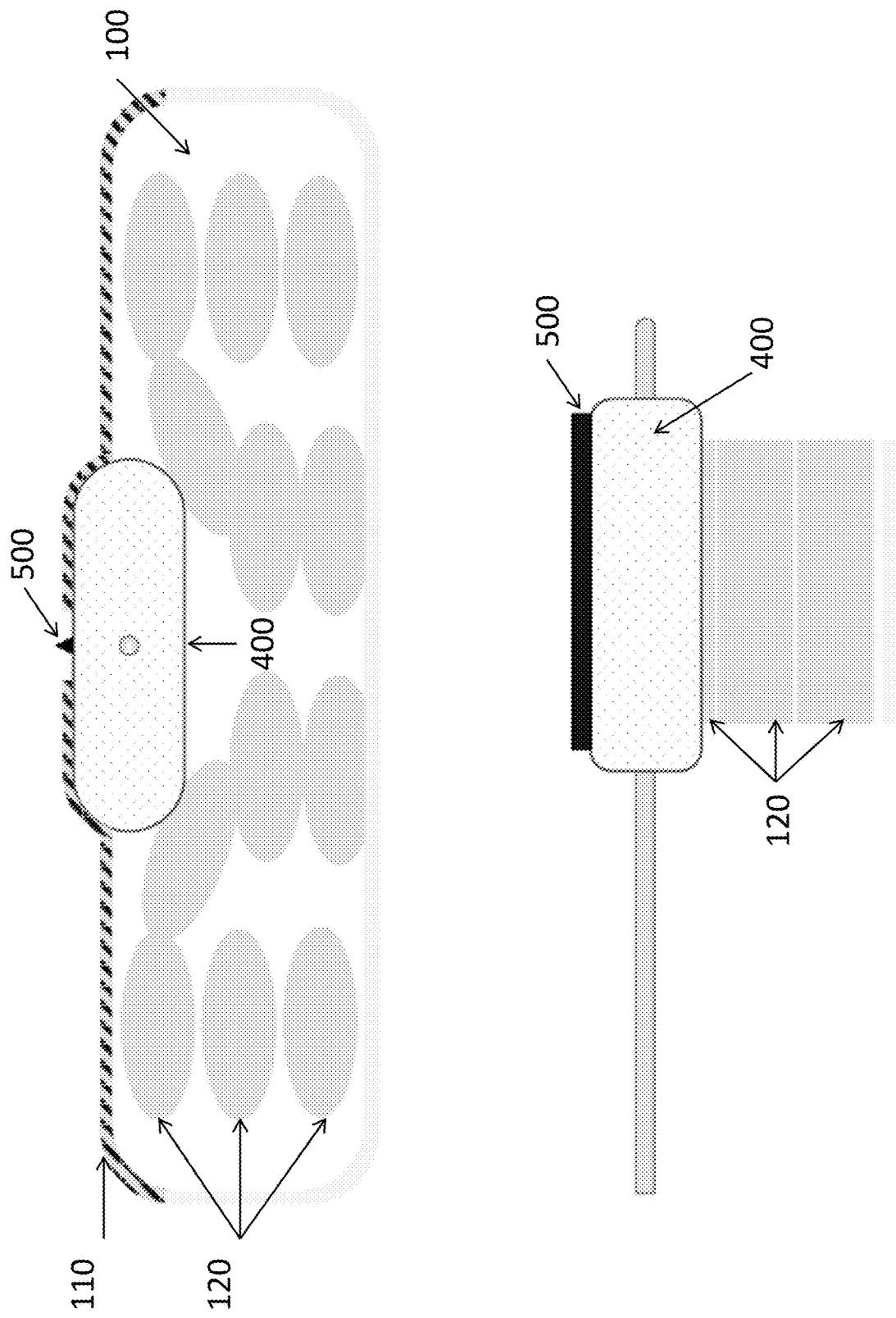

SYSTEMS AND METHODS FOR PERCUTANEOUS DIVISION OF FIBROUS STRUCTURES

CROSS-REFERENCE TO RELATED APPLICATION

This application is a Divisional Application of U.S. patent application Ser. No. 14/958,003, filed Dec. 3, 2015, which claims priority to U.S. Provisional Application Ser. No. 62/086,950, filed Dec. 3, 2014, the disclosure of each of which is hereby incorporated herein by reference in their entireties.

BACKGROUND

The body contains a variety of anatomic compartments with one or more fibrous walls. In certain pathologic situations, the structures within the compartment can be compressed either by swelling or inflammation of the structures or constriction by the compartment walls. For example, compression of blood vessels or nerves passing through the compartment can lead to poor blood flow or loss of neurologic (sensory or motor) function in the tissues within or beyond the compartment. Examples of such conditions include carpal tunnel syndrome, plantar fasciitis, fascial compartment syndrome and abdominal compartment syndrome. The treatment of these conditions will often involve cutting one or more fibrous walls to release pressure on the compartment's anatomic structures. This usually requires open surgery either with direct or endoscopic vision. Few if any percutaneous options exist for these conditions.

Carpal tunnel syndrome (CTS) is the most common cumulative trauma disorder (CTD's) which collectively account for over half of all occupational injuries. It exacts a major economic burden on society including billions in lost wages and productivity. The carpal tunnel is located in the wrist. It's bounded by the carpal bones posteriorly, laterally and medially and by the transverse carpal ligament anteriorly. The flexor tendons and the median nerve pass through the carpal tunnel. Cumulative trauma leads to inflammation within tunnel and manifests itself clinically through its compressive effect on the median nerve resulting it motor and sensory dysfunction in the hand. The diagnosis is usually confirmed with nerve conduction tests. Traditional surgical approaches are effective but invasive and have to be performed in a surgical operating room. An incision is made in the palm or over the wrist. The transverse carpal ligament is surgically exposed and divided with scissors or a scalpel. Endoscopic approaches are less invasive but more technically challenging, have been associated with a higher complication rate and are more expensive. They still require a 1 cm surgical incision and some initial surgical dissection before the endoscope is passed into the carpal tunnel. One device attempts to use a transillumination to guide blind passage of a protected knife. Another device passes a saw-like cutting device into the carpal tunnel blindly or by ultrasound guidance.

It is therefore desirable to have a percutaneous approach to treat carpal tunnel syndrome that is less invasive than existing approaches and that results in less trauma and quicker recovery times for the patient.

SUMMARY

The present disclosure is directed to a device for dividing a fibrous structure. The device may comprise a catheter having a proximal end, a distal end, and lumen extending therebetween; an expandable member positioned near the distal end of the catheter and in fluid communication with the lumen of the catheter; and a cutting element situated on an outer surface of the expandable member.

In various embodiments, the expandable member may be configured to contact the fibrous structure and expand outwards to tension the fibrous structure across the cutting element. The expandable member, in various embodiments, may include a balloon.

The cutting element, in various embodiments, may be configured to apply a mechanical force to weaken or cut the fibrous tissue. Additionally or alternatively, the cutting element, in various embodiments, may be configured to emit electrical or thermal energy to weaken or cut the fibrous tissue. The cutting element may include a blade and/or an electrocautery lead in some embodiments.

The device, in various embodiments, may further comprise at least one sensing element and/or stimulating element on the outer surface of the expandable member. The sensing and/or stimulating elements may be configured to detect or stimulate neuroelectrical in a nearby nerve to facilitate at least one of positioning and orienting the device along the fibrous structure.

The device, in various embodiments, may still further comprise one or more lighting elements situated along a length of the expandable member proximate the cutting element. A brightness and a wavelength of light emitted by the one or more lighting elements may be configured such that the light is visible through subcutaneous tissues and skin, and not visible or visible at significantly lower brightness) through the fibrous wall.

In another aspect, the present disclosure is directed to a method for dividing a fibrous structure. The method may comprise positioning, proximate the fibrous structure, an expandable member having a cutting element situated thereon; expanding the expandable member outwards to tension the fibrous structure across the cutting element; and activating the cutting element to weaken or cut the fibrous structure.

The method, in various embodiments, may further comprise determining whether a nerve is present in the vicinity of the cutting element. This may include at least one of monitoring feedback from the at least one element for signals associated with neurological activity; and emitting, via the at least one element, a signal suitable for stimulating neuroelectrical activity. Determining whether a nerve is present can, in various embodiments, be used to adjust a position and/or orientation of the cutting element.

In yet another aspect, the present disclosure is directed to a method for treating carpal tunnel syndrome. The method may comprise inserting a needle into the carpal tunnel; directing a guidewire through the needle to a position proximate the transverse carpal ligament; advancing, along the guidewire, a device having an expandable member and a cutting element; positioning the cutting element along a portion of the transverse carpal ligament to be divided; expanding the expandable member outwards to tension the transverse carpal ligament across the cutting element; and activating the cutting element to weaken or cut the transverse carpal ligament.

The guidewire, in an embodiment, may be further advanced through the skin and out of the body to provide excellent column strength to facilitate advancement of the device. Ultrasonic imaging and/or illumination, in various embodiments, may be used to facilitate one or more of the steps the method.

Figure 7A:
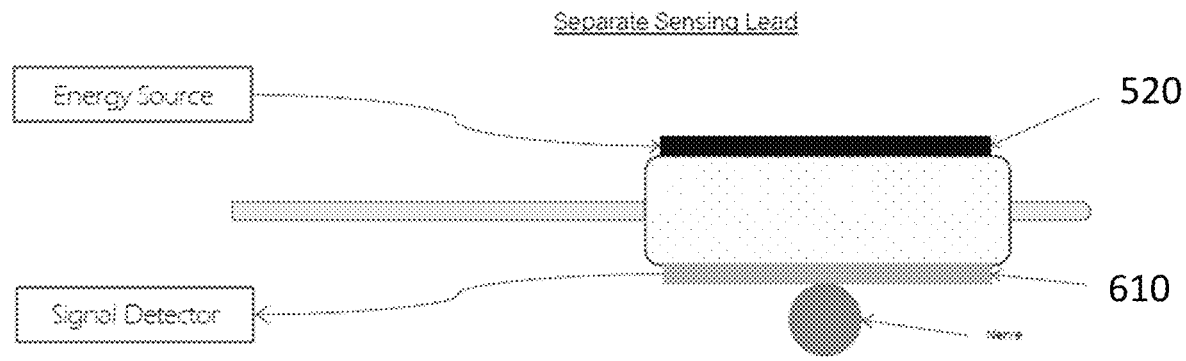
Figure 7B:
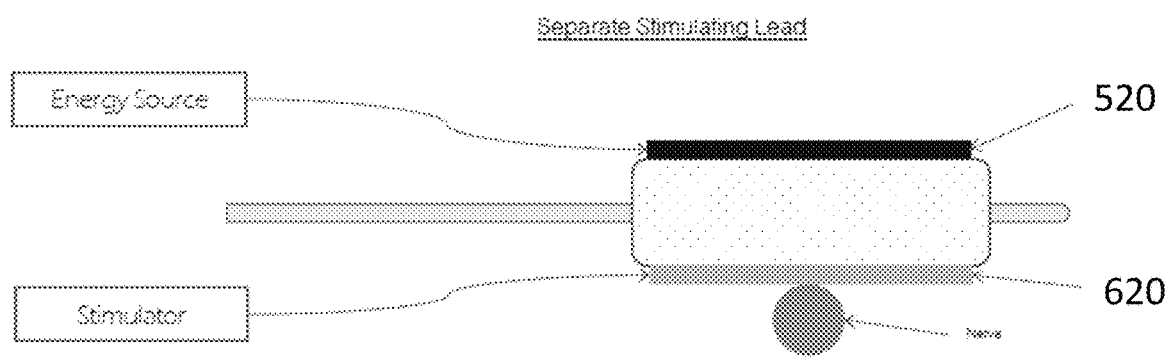
Figure 7C:
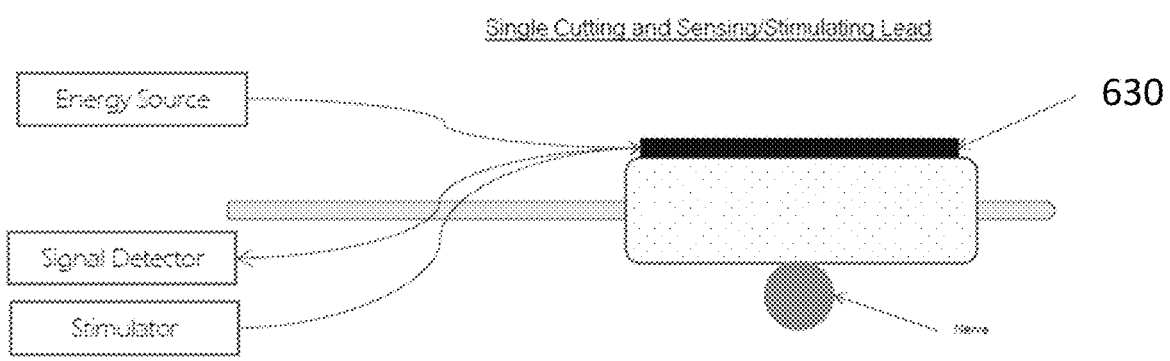
Figure 7D:
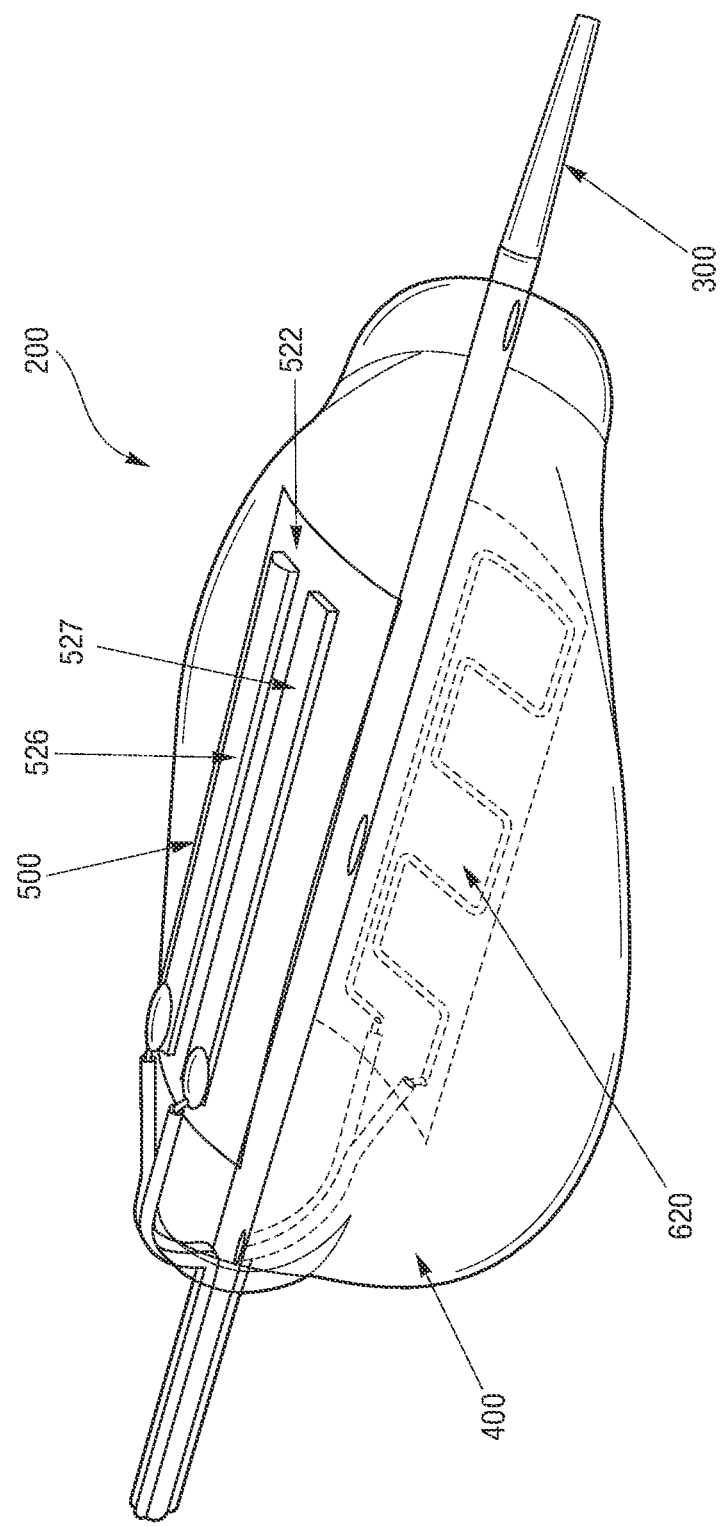
Figure 7E:
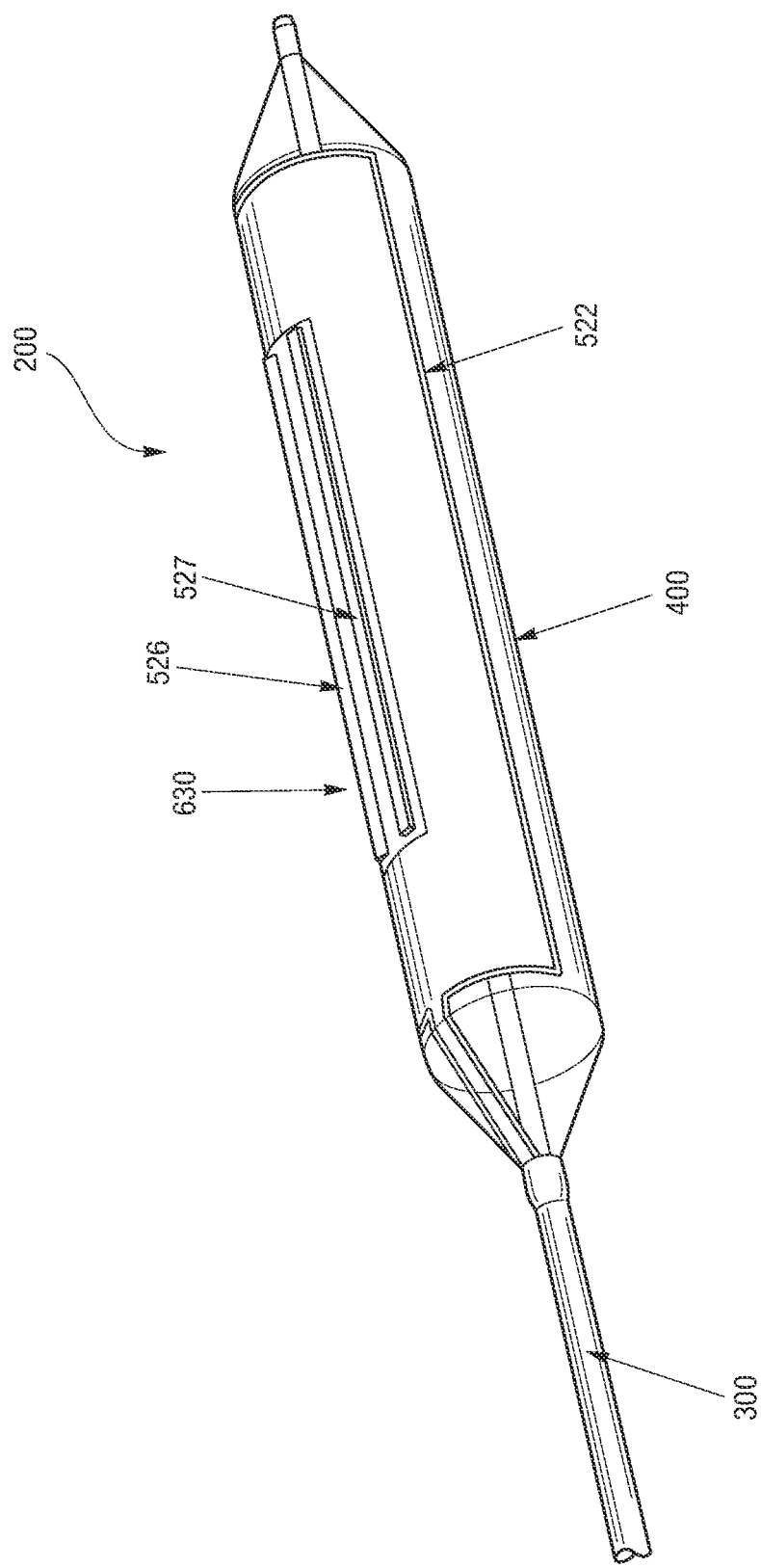
Figure 7F:
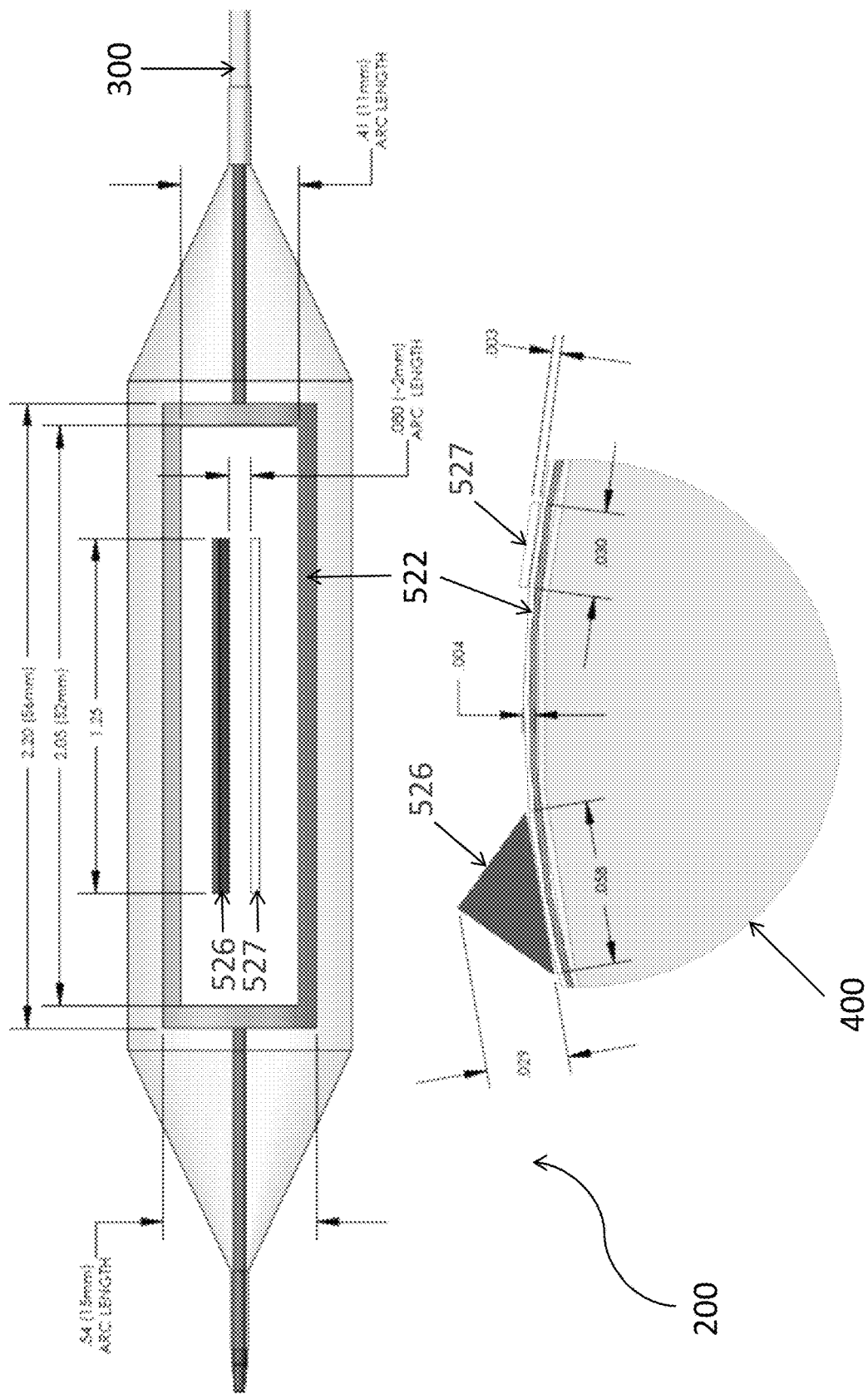
Figure 8A:
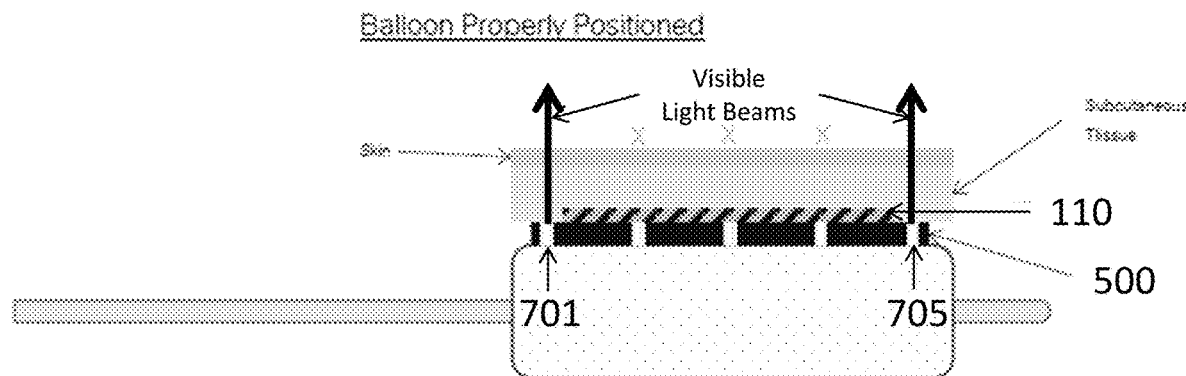
Figure 8B:
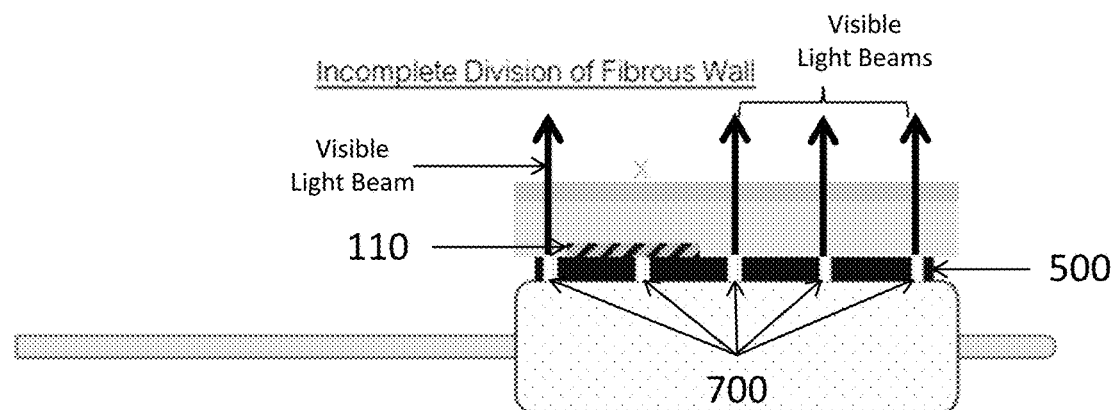
Figure 8C:
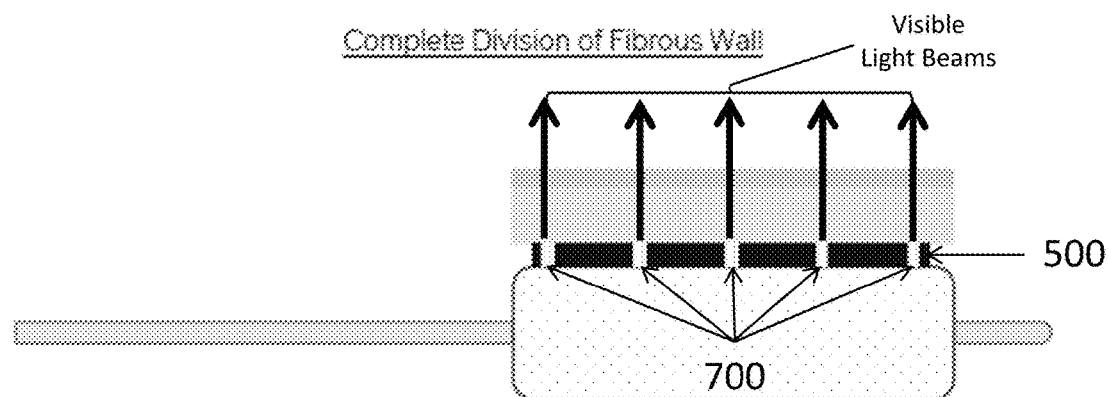
Figure 9A:
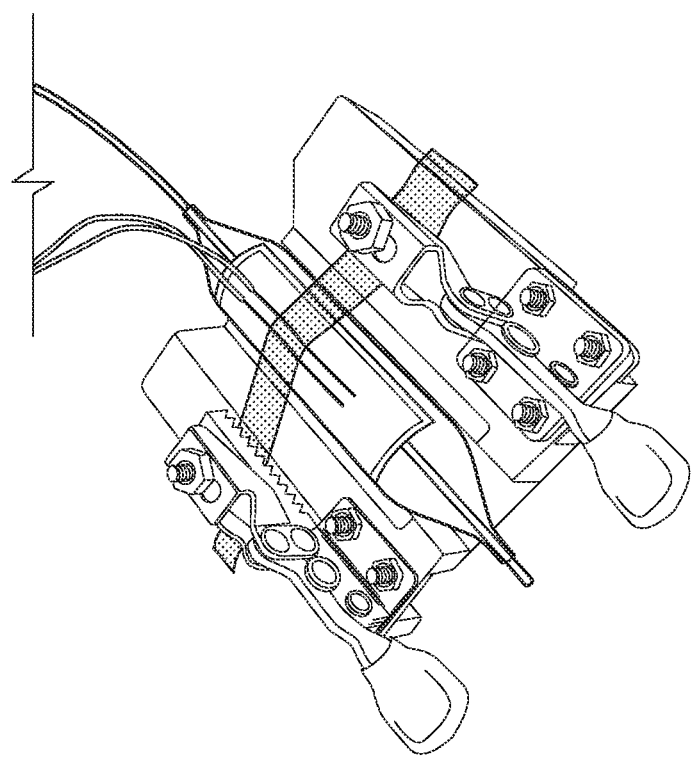
Figure 9C:
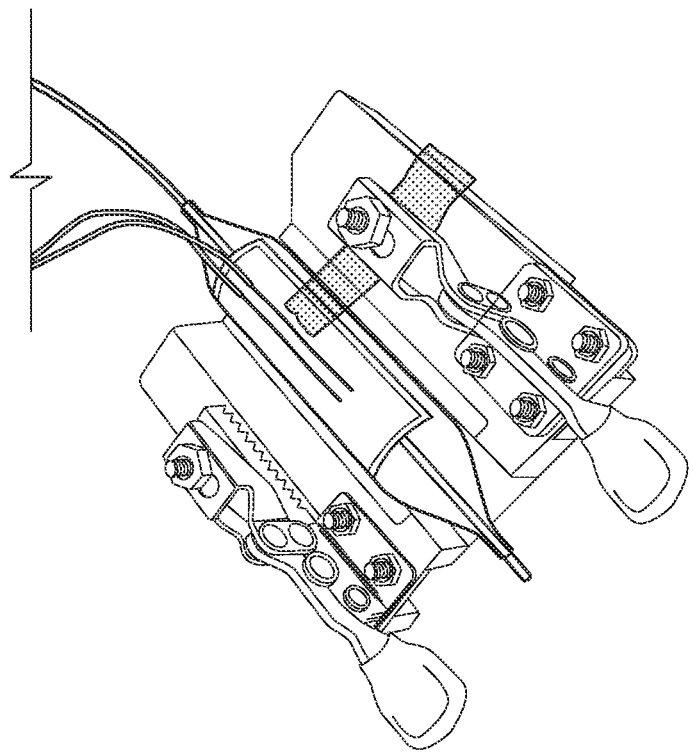
Figure 9B:
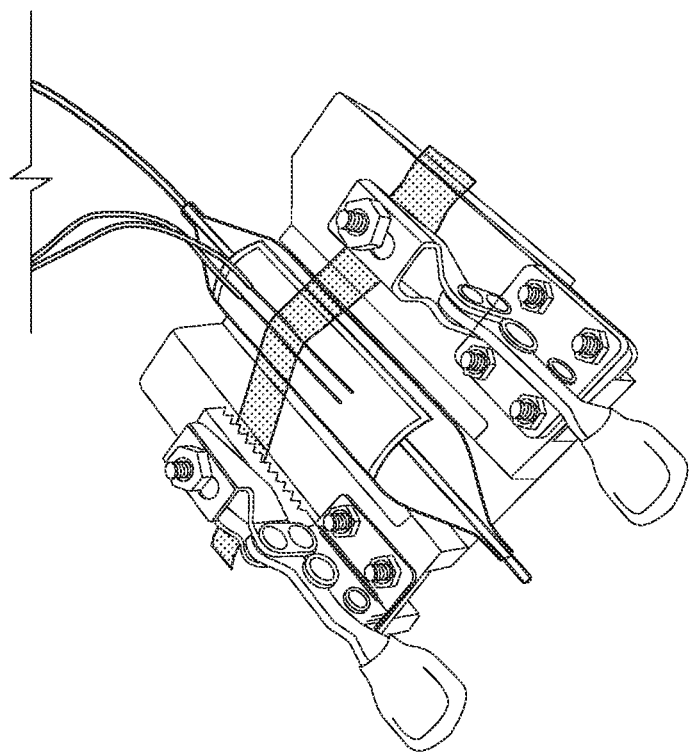
Figure 11A:
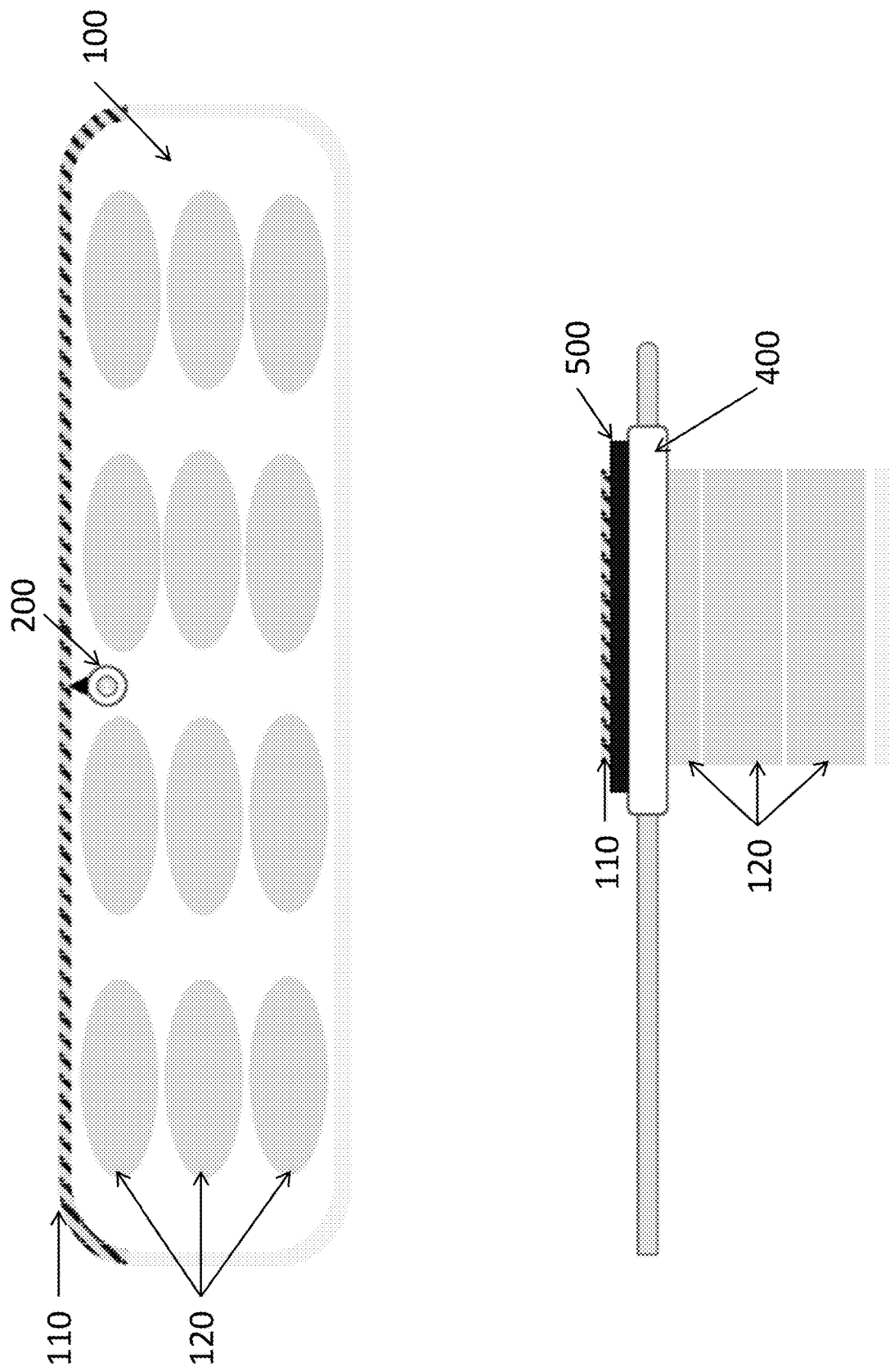
Figure 11C:
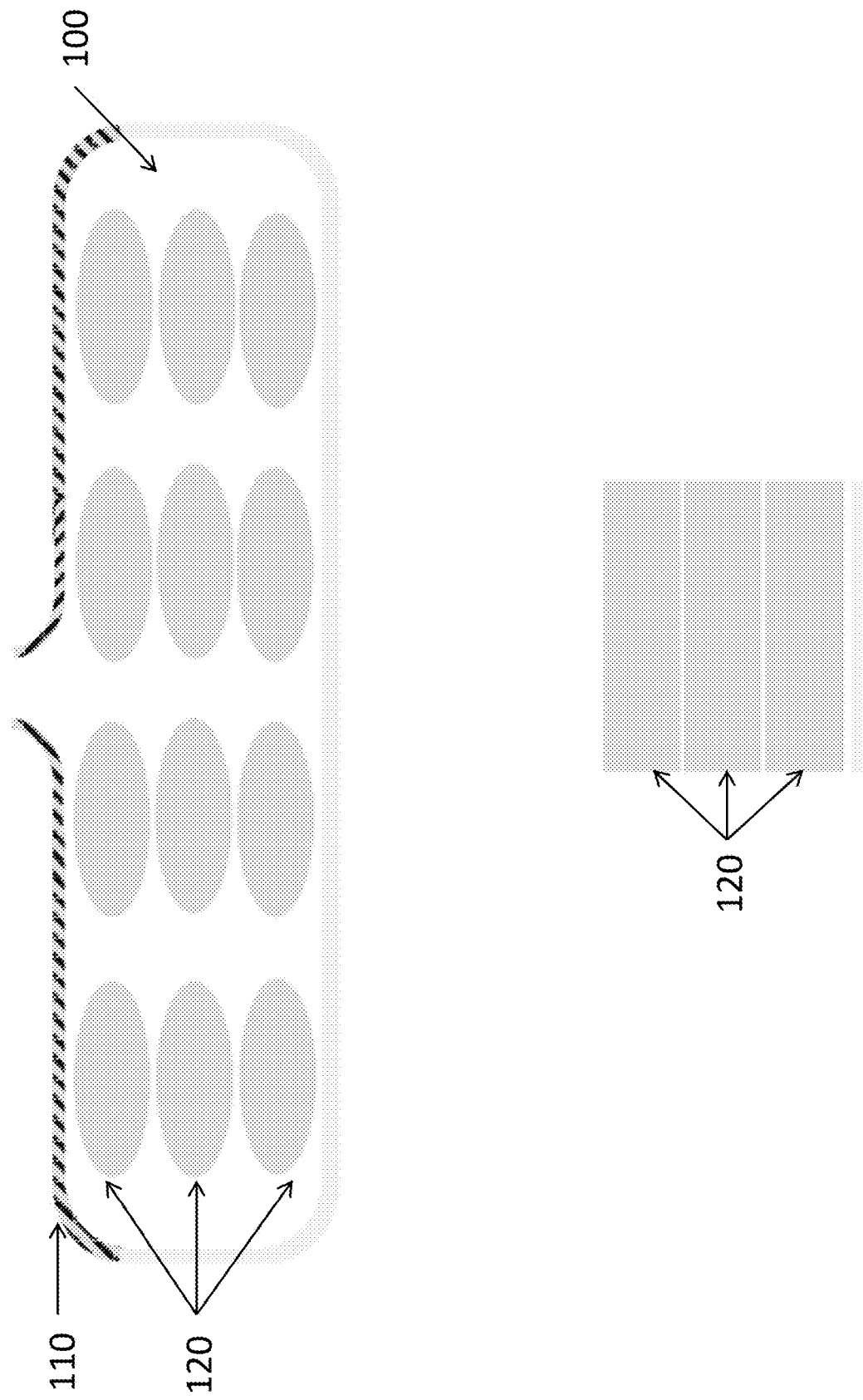
Figure 12A:
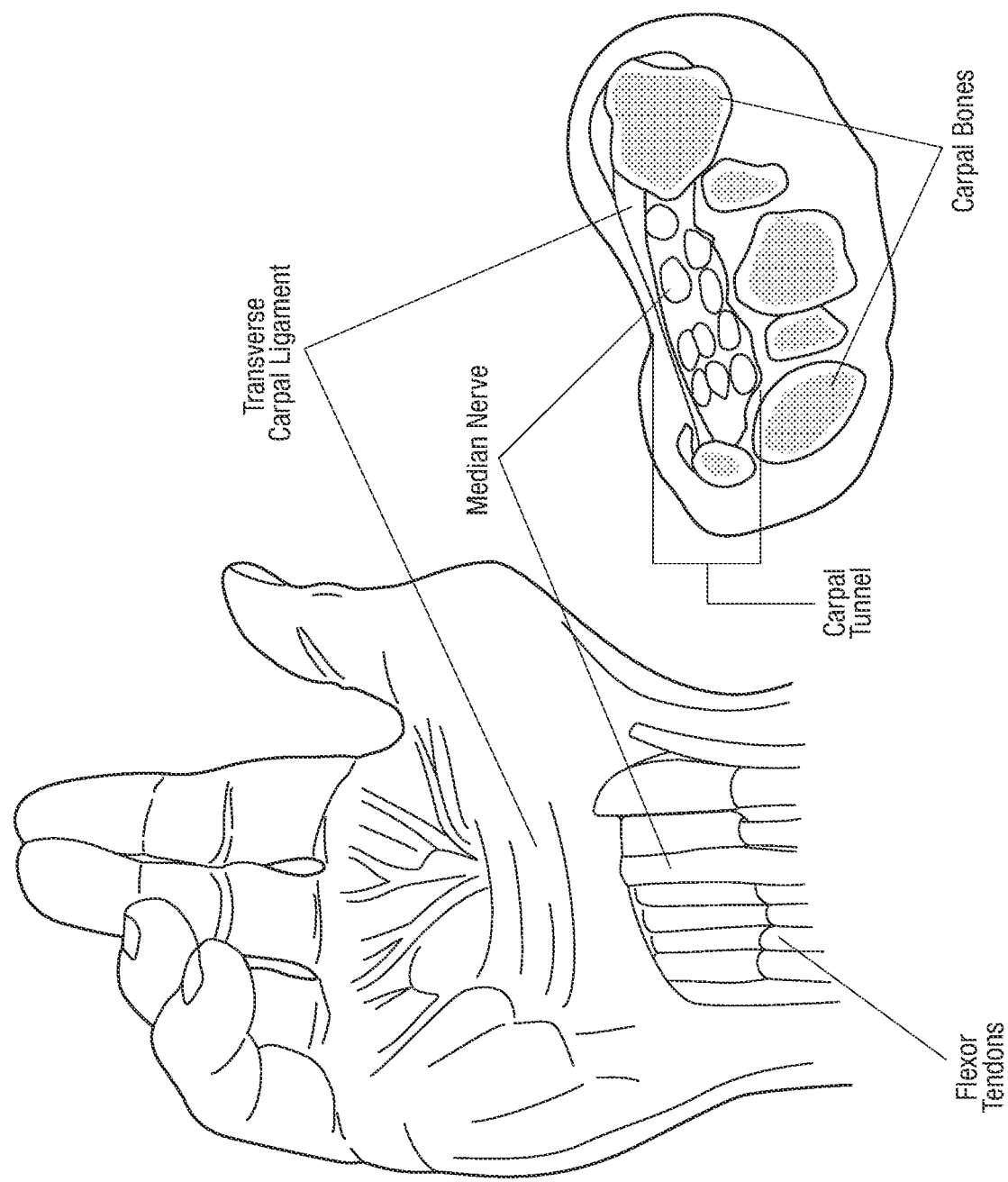
Figure 13:
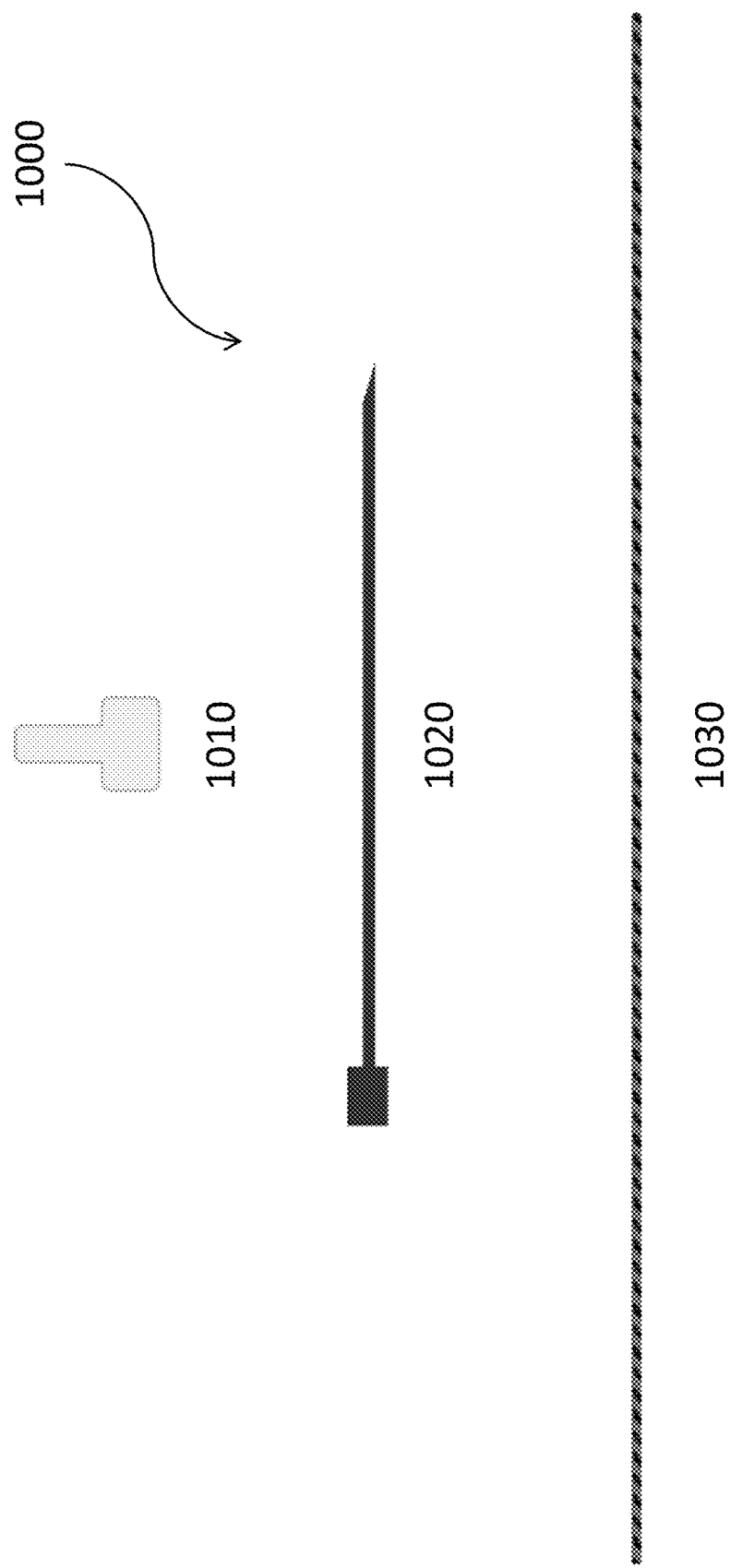

FIGS. $4B_1$-$4B_5$ depict schematic views of various potential cross-sectional shapes of a balloon, in accordance with an embodiment of the present disclosure;

FIGS. 5A and 5B depict a mechanical cutting element of a device for percutaneous division of fibrous structures, in accordance with an embodiment of the present disclosure;

FIGS. 6A-6C depict electrical/thermal cutting elements of a device for percutaneous division of fibrous structures, in accordance with an embodiment of the present disclosure;

FIGS. 7A-7C depict elements for sensing neuroelectrical activity, stimulating neuroelectrical activity, or both, in a nearby nerve, if present of a device for percutaneous division of fibrous structures, in accordance with an embodiment of the present disclosure;

FIG. 7D depicts a perspective view of a device for percutaneous division of fibrous structures, in accordance with an embodiment of the present disclosure;

FIG. 7E depicts a perspective view of a device for percutaneous division of fibrous structures, in accordance with another embodiment of the present disclosure;

FIG. 7F depicts top and cross-sectional schematic views of a device for percutaneous division of fibrous structures, in accordance with another embodiment of the present disclosure;

FIGS. 8A-8C depict schematic views of a device for percutaneous division of fibrous structures having lighting elements, in accordance with an embodiment of the present disclosure;

FIG. 9A depicts an experimental test in which a device for percutaneous division of fibrous structures is used for cutting synthetic tissue, in accordance with an embodiment of the present disclosure;

FIGS. 9B and 9C depict another experimental test in which a device for percutaneous division of fibrous structures is used for cutting bovine pericardium tissue, in accordance with an embodiment of the present disclosure;

FIGS. 10A and 10B depict side and cross-sectional views of a device for percutaneous division of fibrous structures in collapsed and expanded states, in accordance with an embodiment of the present disclosure;

FIGS. 11A-11C depict steps of a method for percutaneous division of fibrous structures, in accordance with one embodiment of the present disclosure;

FIG. 12A depicts a carpal tunnel and associated anatomical structures within the human body;

FIGS. 12B-12F depict steps of a method for treating carpal tunnel syndrome, in accordance with one embodiment of the present disclosure;

FIG. 13 depicts a kit for use in a method for treating carpal tunnel syndrome, in accordance with one embodiment of the present disclosure; and FIGS. 14A-14I depict steps of a method for treating carpal tunnel syndrome using the kit of FIG. 13, in accordance with one embodiment of the present disclosure.

DETAILED DESCRIPTION

Figure 1:
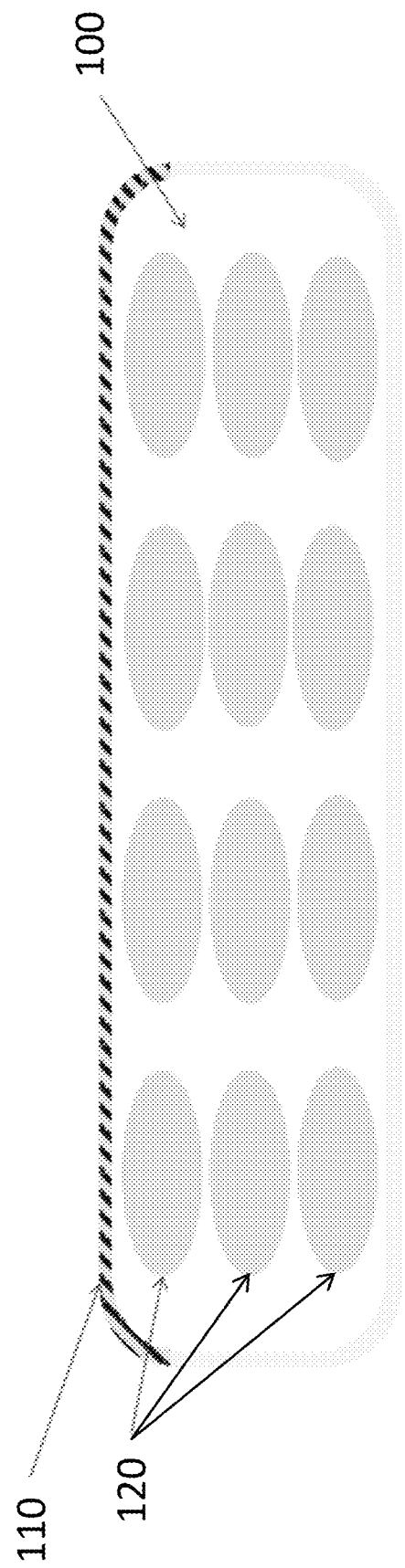
FIG. 1 depicts a schematic view of an anatomical compartment of the human body.

The present disclosure is directed to a medical device, and in particular, devices for percutaneous division of fibrous structures. While the devices and methods described herein may be used for percutaneous division of any sort of fibrous structure within the body, the present disclosure may, from time to time, refer to the treatment of carpal tunnel syndrome as an exemplary application. The carpal tunnel is an anatomic compartment in the wrist bounded by the carpal bones and the transverse carpal ligament. The clinical symptoms of carpal tunnel syndrome primarily arise from compression of the median nerve as it passes through the tunnel. Surgical division of the transverse carpal ligament relieves the compression of the median nerve and its associated symptoms. Referring to FIG. 1, device 200, in various embodiments, may be utilized to divide a fibrous wall 110 of an anatomical compartment 100 within the body to relieve pressure on anatomical structures 120 within compartment 100.

Percutaneous Division Device 200

Figure 2:
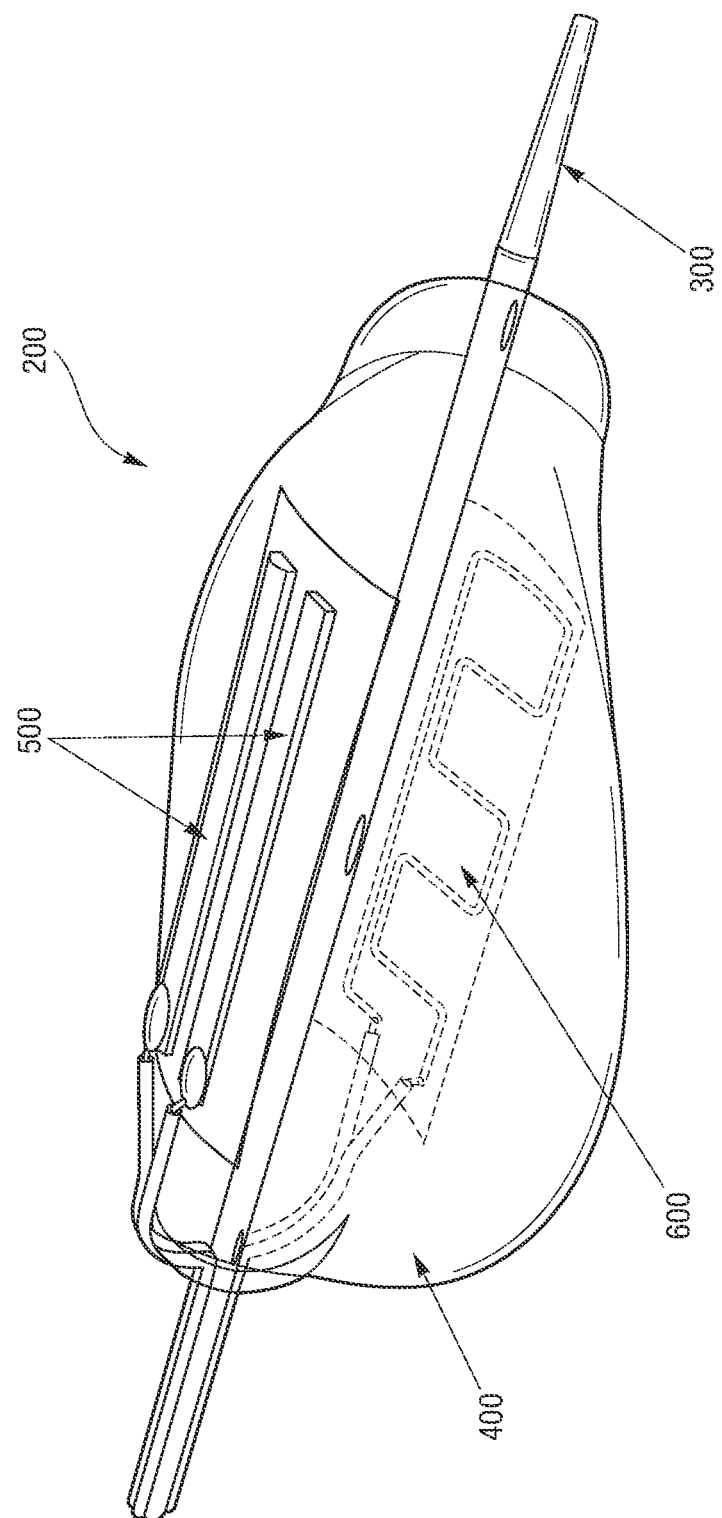
FIG. 2 depicts a device for percutaneous division of fibrous structures, in accordance with an embodiment of the present disclosure.

Referring now to FIG. 2, percutaneous division device 200 of the present disclosure may generally include a catheter 300, an expandable member 400, one or more cutting elements 500, and one or more sensing/stimulating elements 600. Percutaneous division device 200 may be inserted into the body and advanced towards an anatomic compartment 100, such as the carpal tunnel, requiring treatment. Sensing/stimulating element 600 may optionally be utilized to help position device 200 within the compartment, and to avoid damaging any nearby nerves. Once properly positioned within the anatomic compartment, expandable member 400 may be expanded to apply a radial force generating lateral tension along a portion of the fibrous wall of the compartment. Cutting element 500 may be configured to engage the tensioned portion to divide the fibrous wall and thereby decompress the anatomic compartment for therapeutic effect.

Figure 3A:
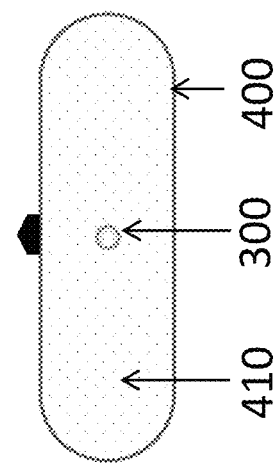
FIGS. 3A and 3B depict side and cross-sectional views of a device for percutaneous division of fibrous structures in deflated and inflated states, in accordance with an embodiment of the present disclosure.
Figure 3A:
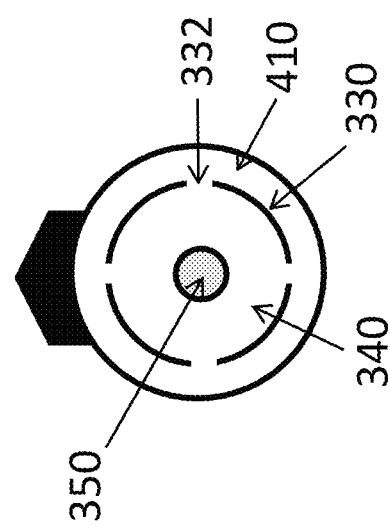
Figure 3A:
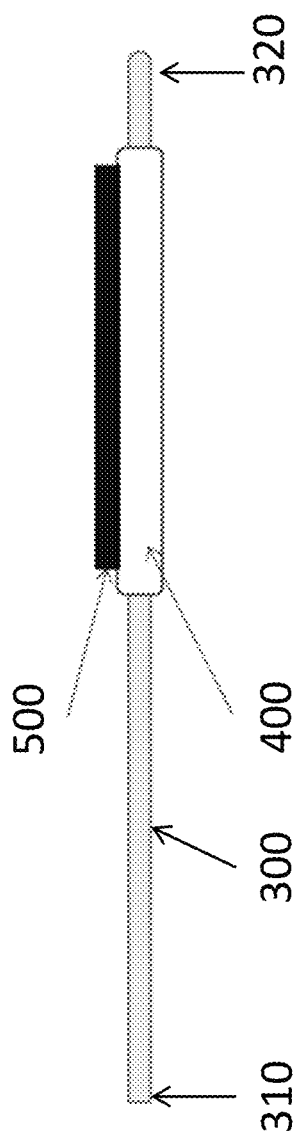
Figure 3B:
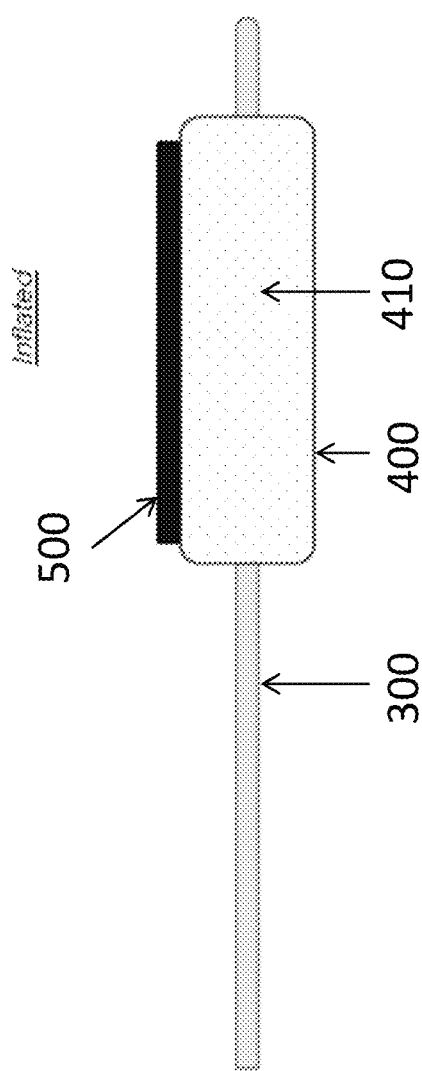

Referring now to the schematic views of FIGS. 3A and 3B, percutaneous division device 200 may include a catheter 300. Catheter 300, in various embodiments, may be rigid, semi-rigid or flexible. Catheter 300 may be made of any biocompatible material including plastic or metal. In embodiment, catheter 300 may be made of a flexible plastic material such as polyurethane, polyethylene or flourothermoplastic, among other suitable plastics.

Catheter 300, as shown, may have a proximal end 310, a distal end 320, and an outer surface 330. Catheter 300, in various embodiments, may include at least one lumen 340 through which fluids may be accommodated and directed between proximal end 310 and distal end 320. Catheter 300 may further include one or more openings 332 (shown in FIG. 3A as side holes) through which fluid may be directed between lumen 340 and an environment situated beyond outer surface 330 outside of catheter 300. Openings 332, in an embodiment, may be situated proximate distal end 320 so as to provide fluid communication between lumen 340 and an interior portion 410 of expandable member 400 positioned about a corresponding portion of outer surface 330 of catheter 300, as shown. In operation, fluid may be introduced into fluid lumen 340 at proximal end 310, directed towards distal end 320, and through openings 332 into interior portion 410 to inflate expandable member 400. Similarly, fluid may be withdrawn from expandable member 400 along the reverse path to deflate expandable member 400. Catheter 300, in various embodiments, may further include at least one lumen 350 for accommodating a guidewire 352 (not shown) for facilitating positioning of catheter 300 within compartment 100.

One of ordinary skill in the art will recognize that these are merely illustrative examples of suitable configurations of catheter 300, and that the present disclosure is not intended to be limited only to these illustrative embodiments.

Still referring to FIGS. 3A and 3B, percutaneous division device 200 may include expandable member 400, such as a balloon or similar expandable structure. For simplicity, expandable member 400 may be referred to herein as balloon 400 in the context of describing percutaneous division device 200; however, it should be recognized that expandable member 400 is not intended to be limited as such. Balloon 400, in an embodiment, may be substantially non-compliant, and can be made of a thin layer or a similar flexible plastic material.

Balloon 400 may be coupled to catheter 300 in a manner suitable for receiving and retaining fluid from lumen 340 of catheter 300 within interior portion 410 of balloon 400. In one such embodiment, balloon 400 may be positioned about a portion of outer surface 330 containing opening(s) 332 such that fluid directed through opening(s) 332 enters interior portion 410 of balloon 400. Balloon 400 may be bonded to catheter 300 to retain fluid directed into its interior portion 410 to allow for inflating balloon 400 during the surgical procedure.

Figure 4A:
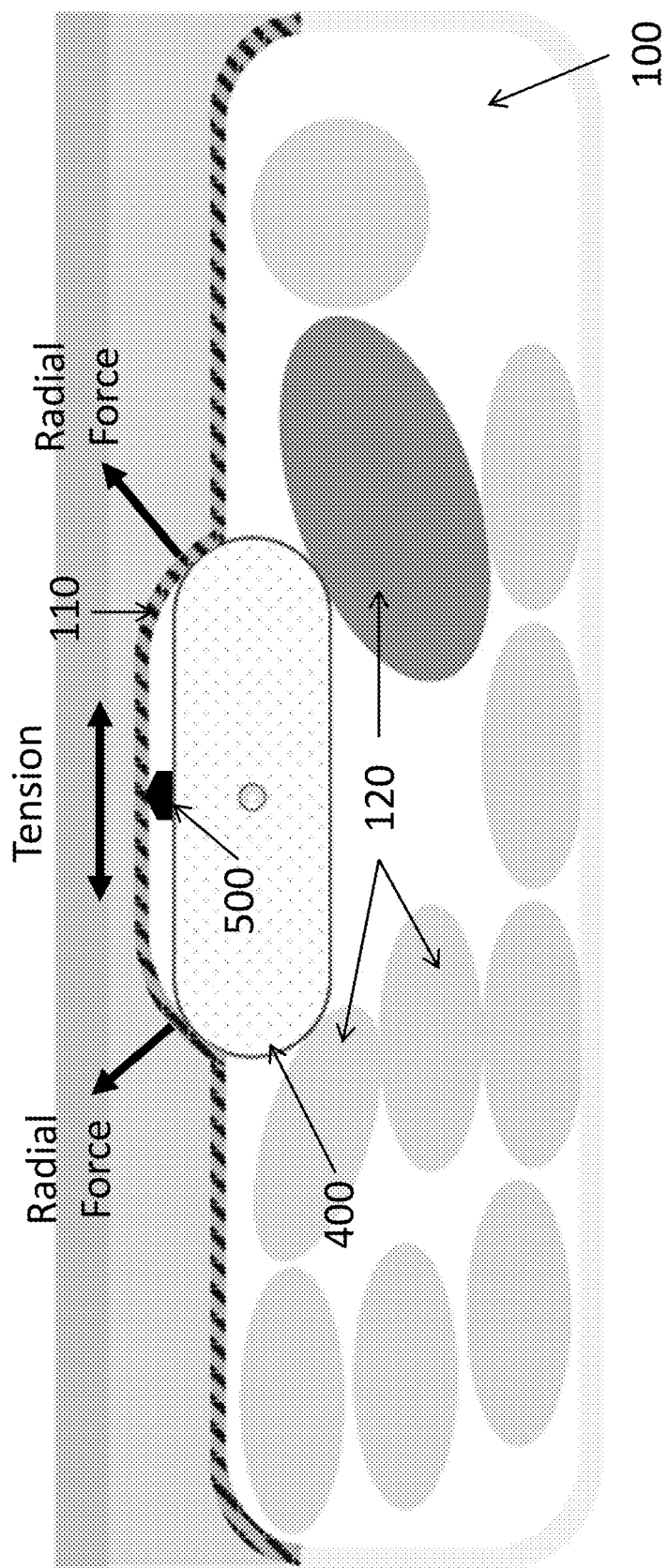
FIG. 4A depicts a schematic view of the device of FIGS. 3A and 3B in an inflated state for tensioning a fibrous wall of an anatomical compartment.

Referring now to FIG. 4A, balloon 400 may be shaped to apply tension to fibrous wall 110. As balloon 400 is inflated, it pushes outward, generating a force in a radial direction on a portion of wall 110, which stretches that portion of wall 110 in a lateral direction. In various embodiments, cutting element 500 may be longitudinally oriented on balloon 400, meaning that the lateral tension created in wall 110 by balloon 400 acts in a direction substantially transverse to the longitudinally-oriented cutting element 500 situated on the surface of balloon 400. As configured, lateral tension causes wall 110 to become taut across cutting element 500, thereby making it easier to divide. In particular, as cutting element 500 weakens a contacted portion of wall 110, tension applied by balloon 400 facilitates division by pulling wall 110 apart along the weakened area. Further, as shown in FIG. 4A, stretching wall 110 taut provides for wall 110 to be contacted by a discrete portion of cutting element 500 (e.g., the tip of cutting element 500, as shown), rather than with a wider portion cutting element 500 as may be the case if wall 110 were slack and allowed to conform around cutting element 500. Stated otherwise, the tension applied by balloon 400 allows cutting element 500 to act with high energy density on a small portion of wall 110, thereby providing for a cleaner cut with less tissue damage, which in turn may reduce the recovery period for the patient.

Still referring to FIG. 4A, balloon 400 may be further shaped and sized to accommodate the specific anatomy of the compartment 100 within which it will be deployed. This may include, for example, being shaped and sized in a manner suitable for manipulating the position of, or minimizing pressure applied to, anatomical structures 120 situated within compartment 100. This may serve to protect these anatomical structures 120 from damage resulting from contact with cutting element 500 and/or to dissect tissues within the compartment to create more space for the anatomic structures within the compartment. As shown in FIG. 4A, in an embodiment, balloon 400 may have an elongated cross-section (e.g., ovular) which, when positioned against fibrous wall 100, provides contact between an elongated side of balloon 400 and fibrous wall 100 that prevents anatomical structures 120 from sliding around its lateral ends and towards the site of division, where they could be damaged by cutting element 500. In another embodiment, balloon 400 may be provided with a substantially circular cross-section (not shown) with a large enough diameter sufficient to push nearby tendons, nerves or other anatomical structures 120 outward from device 200 when inflated.

Referring now to FIGS. $4B_1$-$4B_5$, in other embodiments, balloon 400 may be provided with a variety of other cross sections. For example, balloon 400 may have, without limitation, a substantially circular (FIG. $4B_1$), ovular (FIG. $4B_2$), rectangular (FIG. $4B_3$), or triangular (FIG. $4B_4$) cross sectional shape, to help achieve the desired effect on wall 110 and/or anatomical structures 120. Referring to FIG. $4B_5$, in an embodiment, multiple balloons or shaped members may be positioned in relation to one another to help form the overall shape of balloon 400. Here, one such embodiment illustrates a "pontoon"-like configuration wherein two smaller balloons are positioned on opposing sides of a larger central balloon to help form an overall ovular shape. Of course, one of ordinary skill in the art will recognize any number of additional configurations for this purpose within the scope of the present disclosure.

Similarly, balloon 400 may be adapted to minimize contact with (and applying resulting pressure on) certain surrounding anatomical structures 120 within compartment 100. For example, the small vertical dimension of the elongated cross-sectional design of FIG. 4A may serve to minimize pressure exerted on median nerve 122 situated below the site of division, whilst its longer horizontal cross-sectional dimension may still serve to apply tension to fibrous wall 100 and push tendons 124 aside. Embodiments of balloon 400 may be provided with suitable longitudinal profiles adapted for similar purposes.

Referring now to FIGS. 5A and 5B, percutaneous division device 200 may further include one or more cutting elements 500 situated on balloon 400. The specific orientation of cutting element 500 relative to the axis of the catheter 300 may depend on the specific anatomy of the compartment. Cutting element 500, in various embodiments, may include a mechanical element 510 such as a sharpened blade, as shown in FIG. 5A. In an embodiment, the mechanical element 510 may be provided with a removable cover 512 to protect surrounding tissue during positioning of device 200 and exposed just prior to balloon inflation, as shown in FIG. 5B. In another embodiment, the mechanical element 510 may be sheathed within catheter 300 and advanced once balloon 400 is inflated (not shown). In operation, when balloon 400 is inflated, the mechanical element 510 makes contact with the fibrous wall 110. As the pressure in balloon 400 further increases, the axial and radial forces tension the fibrous wall 110, and the radial force pushes mechanical element 510 through the fibrous wall 110, thereby dividing fibrous wall 110 and relieving the pressure in compartment 100, as described in more detail later in the disclosure.

Referring now to FIGS. 6A-6C, cutting element 500, in various other embodiments, may include an electrical element 520 configured to utilize electrical and/or thermal energy to divide fibrous wall 100. For example, cutting element 520 may include a unipolar or bipolar leads configured to communicate electrically with an electrocautery generator, as shown in FIGS. 6A and 6B, respectively. In operation, when balloon 400 is inflated and the electrocautery lead(s) is in contact with fibrous wall 110, the electrocautery generator may be activated to deliver radiofrequency energy to the electrocautery lead(s). The radiofrequency energy heats and cuts the contacted, tensioned portion of the fibrous wall 110 and the fibrous wall 110 is divided under the pressure of balloon 400, thereby relieving the pressure in compartment 100, as described in more detail later in the disclosure. A bipolar configuration may be preferable in anatomic areas with critical structures (nerves, blood vessels) in the vicinity, as it limits the thermal spread of the radiofrequency energy. Leads 520 attached to alternative energy sources, such as microwave and laser light, may also be applicable in certain applications. As later shown in FIGS. 7E and 7F, percutaneous division device 200 may further comprise a layer of insulating material 522 situated between cutting element 520 and balloon 400, so as to protect balloon 400 from heat-related damage when cutting element 500 is energized.

Embodiments of cutting element 520 utilizing electrical and/or thermal energy for division, in an embodiment, may further have a sharp knife-like edge (not shown) so that fibrous wall 110 is divided using both electrical and mechanical means. Similarly, referring FIG. 6C, lead(s) 520 may be provided with a substantially triangular cross-section. As configured, the leading edge 522 of the triangularly-shaped lead 520 may serve to concentrate the electrical and mechanical, thereby providing highly-concentrated energy density along a fine line at the site of division. This may result in less tissue trauma, shorter cutting times, faster recovery times, and more precise division of the fibrous wall 100. Further, the sloping surfaces 524 of the triangularly-shaped lead 520 may serve to further spread (i.e., tension) the portion of fibrous wall 100 proximate leading edge 522, thereby further enhancing the ability of device 200 to cut and divide fibrous wall 110. Further, a portion of the surface of the lead 520 extending up sloping surfaces 254 may be coated with an insulating material, allowing further concentration of the energy density to leading edge 522.

Referring now to FIGS. 7A-7C, percutaneous division device 200 may further include one or more elements 600 configured for sensing neuroelectrical activity, stimulating neuroelectrical activity, or both, in a nearby nerve, if present. Such elements may be utilized to determine whether balloon 400 and cutting element 500 are positioned appropriately relative to structures within compartment 100.

As shown in FIG. 7A, in an embodiment, element(s) 600 may include sensing element(s) 610 configured to detect nerve conduction. As configured, an operator may utilize feedback from sensing element(s) 610 to determine whether cutting element 500 may be in the vicinity of a nerve, such as the median nerve in the carpal tunnel. Sensing element 610 may be connected to an electrical signal detector. Sensing element 610 may be designed to detect an electrical signal emanating from a nearby nerve (e.g., the median nerve) at baseline or from activation of motor nerve fibers during normal muscle contraction (e.g., hand grip) or during electrical stimulation of the nerve (e.g., in the forearm), similar to how nerve conduction studies are performed. A positive signal would confirm that the nerve is located away from cutting element 520.

As shown in FIG. 7B, In another embodiment, element(s) 600 may include stimulating element(s) 620 configured to emit a signal for stimulating nearby nerves. Simulating element 620 may be configured to function in an analogous manner as commonly utilized nerve stimulators used in anesthesia to assess successful pharmacologic muscle relation. An electrical stimulus may be delivered to the nerve by stimulating element 620. If stimulating element 620 is in the vicinity of a nerve, a corresponding motor reaction is noted in the muscles supplied by the nerve such as twitching of the hand from stimulation of the median nerve. A positive response to stimulation would provide confirmation that the nerve is located away from cutting element 520.

In yet another embodiment (not shown), element(s) 600 may include a sensing element(s) 610 and a separate stimulating element(s) 620. In still another embodiment (not shown), element(s) 600 may include a hybrid element configured for both sensing and stimulating functionality (not shown).

Referring to FIG. 7C, in a further embodiment, element(s) 600 may include an element 630 configured for cutting functionality, and at least one of sensing and/or stimulating functionality. Stated otherwise, element 630 may be a hybrid element configured to be a cutting element 500, and at least one of a sensing element 610 and stimulating element 620. Element 630 may initially be utilized as a sensing element 610 and/or stimulating element 620 to facilitate positioning as described above. Once the operator confirms that the nerve is not in the vicinity of cutting element 500, element 630 can be used as a cutting element 500 to mechanically, electrically, or thermally weaken or cut fibrous wall 110. Element 630 can be a single lead, where its functionality as a sensing, stimulating or cutting element is determined by whether it electrically communicates with a signal detector, stimulator or cutting energy source.

A layer of insulating material, in various embodiments, may be situated between element(s) 600 and balloon 400, so as to protect balloon 400 from heat-related damage when element(s) 600 are energized.

Referring to FIG. 7D in an embodiment, percutaneous division device 200 may include an expandable member 400 in relation to a catheter 300 with a stimulating element 620 located on the inferior surface of the expandable member 400 and a cutting element 500 located on the superior surface off the expandable member. The cutting element 500 is separated from the expandable member 400 by a layer of insulating material 522 which protects the expandable member 400 from damage from heat generated by the cutting element 500. The cutting element 500 in this embodiment is a bipolar lead with and triangular active lead 526 and a flat passive return lead 527, Referring to FIGS. 7E and 7F in an embodiment, percutaneous division device 200 may include an expandable member 400 in relation to a catheter 300 with a hybrid element 630 located on the superior surface of the expandable member 400. The hybrid element 630 is separated from the expandable member 400 by a layer of insulating material 522 which protects the expandable member 400 from damage from heat generated by the hybrid element 630. The hybrid element 630 in this embodiment is a bipolar lead with and triangular active lead 526 and a flat passive return lead 527. In stimulating mode, either or both leads can be used to deliver a stimulating signal to confirm that the nerve is not in the vicinity of the hybrid element. I cutting mode the bipolar electrical energy is delivered between the active lead 526 and the return lead 527.

Depending on the positioning of element(s) 600 on balloon 400, and on known anatomy, the operator may further determine whether device 200 is properly positioned. For example, in a carpal tunnel surgical procedure, it may be desired to position device 200 between the transverse carpal ligament (i.e., fibrous wall 110) and the median nerve (i.e., nerve 122), with cutting element 500 (or hybrid element 630) directed towards the transverse carpal ligament. If element(s) 600 are positioned proximate cutting element 500 and provide feedback indicating that the nerve is in that vicinity, an operator may deduce that: 1) balloon 400 is properly oriented, but improperly positioned under the median nerve, rather than between it and the transverse carpal ligament, or 2) balloon 400 is properly positioned, but improperly oriented with cutting edge 500 facing the median nerve rather than the transverse carpal ligament. Similarly, in embodiments where element(s) 600 are positioned on an opposing side of balloon 400 from cutting element 500, the operator may make similar, albeit opposite, deductions. To that end, it should be apparent to one of ordinary skill in the art that any suitable number, combination, and arrangement of element(s) may be utilized for any given application to provide suitable feedback for facilitating placement of balloon 400 and cutting element 500 within compartment 100, and that the present disclosure is not intended to be limited to any such exemplary embodiments thereof provided herein.

Referring now to FIGS. 8A-8C, as an additional or alternative feature for facilitating use, percutaneous division device 200 may include one or more lighting elements 700 along the length of balloon 400 in the vicinity of cutting element 500, as shown in FIGS. 8A-8C. The brightness and wavelength of the row of lighting elements 700 may be configured such that they can be visualized through the subcutaneous tissues and skin but not visualized (or visualized at significantly and discernibly lower brightness) when place below fibrous wall 110. As such, when the balloon is positioned below fibrous wall 110 and the lighting elements 700 are activated, and the length of fibrous wall 110 relative to the length of cutting element 500 on balloon 400 can be determined by assessing which light elements 700 shine through the tissues. In an embodiment, the row of lighting elements 700 can be longer than the length of fibrous wall 110 so that lighting elements 701 and 705 at the proximal end and distal end of balloon 400 can shine through to help determine the relative length of the tissue. Once cutting element 500 is activated, the completeness of the fibrous wall division can be assessed. A complete division would be indicated if all light elements 700 shine through. If the division is incomplete, one or of the light elements 700 will remain dark and the operator can make another attempt to completely divide fibrous wall 110. In addition, should balloon 400 and hence cutting element 500 be relatively shorter than the length of fibrous wall 110, multiple divisions along the length of fibrous wall 110 can be employed. Although disclosed as having a plurality of lighting elements 700 along the length of balloon 400, it should be appreciated that one lighting source 700 extending the length of balloon 400 can be used.

Referring now to FIGS. 9A-9C, synthetic and bovine tissues were divided during testing with a prototype of an embodiment of percutaneous division device 200. The prototype device comprised a 20 mm balloon, inflated with water to 5 atm, with polyimide and PEEK film material situated between electrodes and the balloon surface to provide insulation. A bipolar arrangement of electrodes made from coated flat-wire were spaced 2 mm apart and mounted vertically on the insulating material to simulate a triangular shaped cutting element. Referring first to FIG. 9A, a strip of SynDaver synthetic tissue was placed laterally across the prototype device and tensioned to a level representative of the transverse carpal ligament of the carpal tunnel. A full cut through the SynDaver synthetic tissue was produced by energizing the electrode with 20 W of power. Referring to FIGS. 9B and 9C, a second test using similar setup, only with bovine pericardium tissue, was performed using the prototype device. As shown in FIG. 9C, a full cut through the bovine pericardium tissue was produced with 20 W of power.

Percutaneous Division Device 800

FIGS. 10A and 10B illustrate percutaneous division device 800 of the present disclosure. Device 800 may generally include similar components as device 200, and may additionally or alternatively comprise an expandable member 900 configured for expanding and contracting via mechanical actuation.

Expandable member 900 may comprise a surface 910 on which cutting element 500 and (if equipped) sensing/stimulating elements 600 may be situated as in device 200. In various embodiments, surface 910 may be made of a flexible material capable of collapsing when device 800 is in a non-actuated state, and expanding when device 800 is in an actuated state. In an embodiment, surface 910 may be a balloon or other membrane formed of a flexible material.

Expandable member 900 may further comprise support members 920 configured to expand surface 910 when device 800 is in an actuated state, and to collapse surface 910 when device 800 is in a non-actuated state, similar to the way fluid may be used to inflate and deflate expandable member 400 of device 200. In various embodiments, support members 920 may include ribs or similar structure configured to press radially outwards on surface 910 in an expanded state. In an embodiment, support members 920 may be formed of a shaped-material that springs outwards when a retaining force is released so as to expand surface 910. In another embodiment, support members 920 may be configured to spread outwards and collapse inwards under mechanical actuation.

In various embodiments, expandable member 900 may be actuated via a mechanism 362 extending through a lumen 360 in catheter 300. Mechanism 362, in an embodiment, may include an elongated shaft 364 coupled to support members 920. In an embodiment, elongated shaft 364 may be actuated (e.g., pushed or pulled in an axial direction) that causes support members 920 to spread radially or collapse axially to expand and collapse expandable member 900, respectively.

In various other embodiments, device 800 may include a sheath (not shown) or similar mechanism configured to be placed over expandable member 900 to retain, in a collapsed state, support members 920 made of shaped-material. The sheath may be retracted to expose expandable member 900, thereby allowing support members 920 to spring outwards so as to expand surface 910 into a desired shape.

Support members 920 may be configured to provide expandable member 900 with a suitable cross-sectional shape (e.g., circular, elongated, etc.) for accommodating the specific anatomy of the compartment 100 within which device 800 will be deployed, for applying tension to fibrous wall 110 of the compartment 100, and or for manipulating the position of, or minimizing pressure applied to, anatomical structures 120 situated within compartment 100, as previously described.

Methods for Percutaneous Division of Fibrous Structures

FIGS. 11A-11C illustrate methods for percutaneous division of a fibrous wall 110 of an anatomical compartment 100 using various embodiments of device 200.

Referring first to FIG. 11A, device 200, with balloon 400 in a deflated state, may be inserted into the body and advanced into anatomical compartment 100. Device 200 may be navigated into a position proximate fibrous wall 110, and oriented such that cutting element 500 is pointed towards fibrous wall 110 and away from other critical structures, such as anatomical structures 120. The positioning and orientation of cutting element 500, at this stage, may be confirmed by inspection, lighting elements 700, an imaging modality, a sensing/stimulating functionality 600, or in other suitable manner, as previously described.

Referring now to FIGS. 11B and 11C, after confirming that cutting element 500 is properly positioned and oriented, a fluid such as saline or a contrast material may be directed through inflation lumen 340 of catheter 300 and into interior portion 410 of balloon 400 to inflate balloon 400.

In embodiments of device 200 comprising mechanical cutting element 510 (as shown), inflation may continue until building pressure within balloon 400 causes mechanical cutting element to engage fibrous wall 110 with suitable force to weaken and thereby divide fibrous wall 110 under the simultaneously-building tension provided by balloon 400.

In embodiments comprising electrical and/or thermal cutting elements 520 (not shown), balloon 400 may first be inflated to a pressure sufficient to tension fibrous wall 110 to a desired level, at which point cutting elements 520 may then be energized to weaken fibrous wall 110 and thereby divide it under the tension provided by balloon 400.

In various embodiments, the position and orientation of cutting edge 500 may be rechecked throughout the inflation process. In one such embodiment, balloon 400 may be partially inflated to a first pressure suitable to give it some shape, at which point a recheck of position and orientation is performed before continuing. This may be repeated any number of suitable times during the inflation process to ensure that fibrous wall 110 is divided properly, and without causing damage to anatomical structures 120.

Complete division of fibrous wall 110, in various embodiments, may be confirmed by inspection, lighting elements 700 (as previously described), an imaging modality, or some other suitable technique (e.g. measuring a corresponding reduction in balloon pressure associated with dividing fibrous wall 110 and relieving the pressure within anatomical compartment 100).

Of course, one of ordinary skill in the art will recognize that embodiments of device 800 may be utilized to divide fibrous wall 110 in a similar fashion. In various embodiments, rather than inflating expandable member 400 with fluid to tension fibrous wall 110 (and, if equipped, engage fibrous wall 110 with mechanical cutting element 510 to weaken it), expandable member 900 of device 800 may be expanded mechanically, as previously described. As with device 200, expansion of expandable member 900 may be performed in a controlled manner so as to provide intermediate opportunities to recheck the positioning and orientation of cutting element 500 relative to fibrous wall 110 and anatomical structures 120 so as to ensure that fibrous wall 110 is divided properly and without causing collateral damage.

Methods for Treatment of Carpal Tunnel Syndrome

Figure 12B:
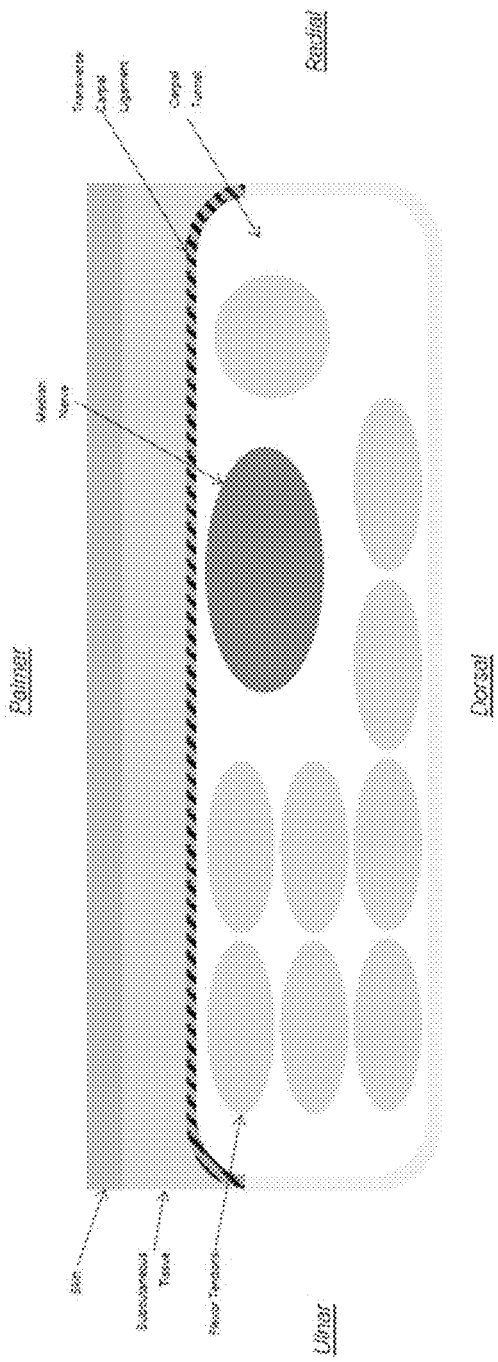

Embodiments of devices 200, 800 may be particularly well-suited for treating carpal tunnel syndrome by dividing the transverse carpal ligament. Referring to FIGS. 12A and 12B, the carpal tunnel is an anatomic compartment in the wrist bounded by the carpal bones and the transverse carpal ligament. The clinical symptoms of carpal tunnel syndrome primarily arise from compression of the median nerve as it passes through the tunnel. Surgical division of the transverse carpal ligament relieves the compression of the median nerve and its associated symptoms. Embodiments of devices 200, 800 are capable of dividing the transverse carpal ligament percutaneously. In addition, expandable members 400, 900 may, in operation, dissect and mobilize the median nerve and tendons away from the transverse carpal ligament, thereby enhancing the decompression of the carpal tunnel and potentially preventing late scarring and recurrent symptoms. For ease of explanation, the following methods for treatment of carpal tunnel syndrome will be explained in the context of using device 200, though it should be recognized that similar methods may be employed using device 800 within the scope of the present disclosure.

Figure 12C:
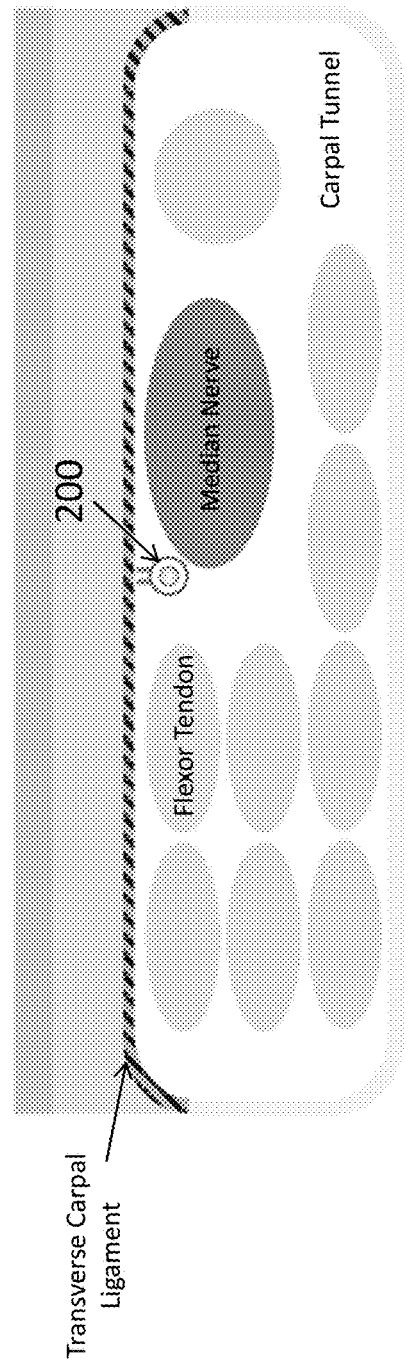

Referring now to FIG. 12C, device 200, with balloon 400 in a deflated state, may be inserted into the body and advanced into the carpal tunnel. Device 200 may be navigated into a position proximate the transverse carpal ligament, and oriented such that cutting element 500 (shown here as an electrical and/or thermal cutting element 520) is pointed towards the transverse carpal ligament and away from other critical structures, such as the median nerve and surrounding flexor tendons. Embodiments of device 200 may be of suitable dimensions for positioning within the carpal tunnel in proximity to the transverse carpal ligament. The positioning and orientation of cutting element 500, at this stage, may be confirmed by inspection, lighting elements 700, an imaging modality, a sensing/stimulating functionality 600, or in other suitable manner, as previously described.

Figure 12D:
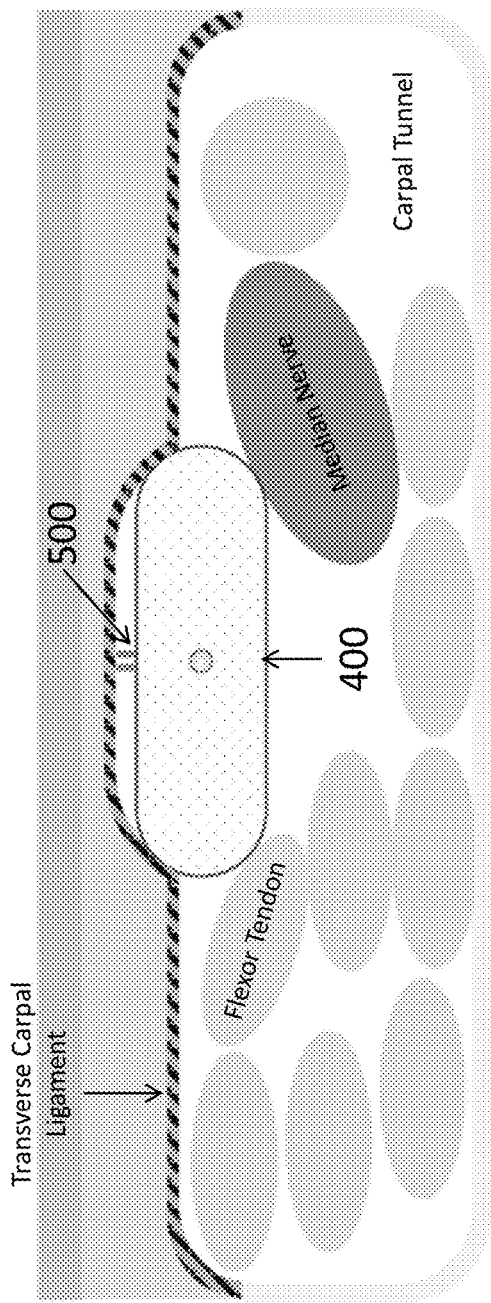

Referring now to FIG. 12D, after confirming that cutting element 500 is properly positioned and oriented relative to the transverse carpal ligament and surrounding anatomical structures such as the median nerve and flexor tendons, balloon 400 may be inflated. Expandable member 400 may be configured to expand to dimensions appropriate for use within the carpal tunnel. Embodiments of balloon 400 having an elongated cross-sectional shape, or other suitable shape, may act to dissect the transverse carpal ligament off the carpal tunnel contents during inflation, creating space and enhancing the decompression of the carpal tunnel. In such an embodiment, balloon 400 can be made of a substantially noncompliant material and may be inflated to a specified pressure, designed to achieve this dissecting effect and to provide enough radial force to stretch the transverse carpal ligament across cutting element 500 for subsequent division. As shown in FIG. 12D, the inflated balloon 400 has dissected and pushed the median nerve and some of the flexor tendons away from one another, and away from cutting element 500. The inflated balloon 400 has also applied sufficient tension to the transverse carpal ligament such that it is stretched taut across cutting element 500.

Figure 12E:
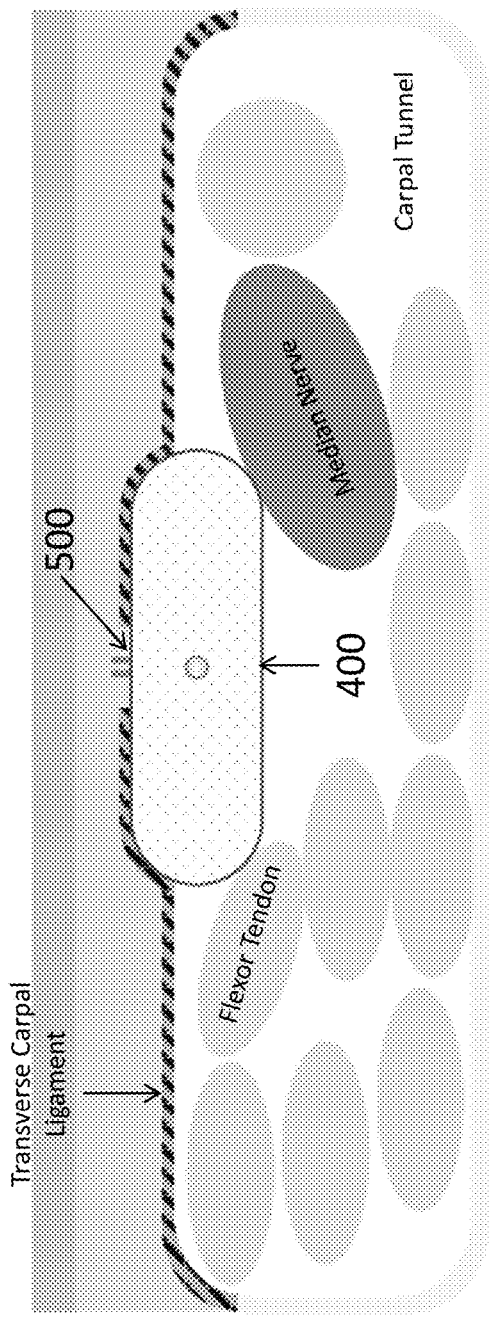
Figure 12F:
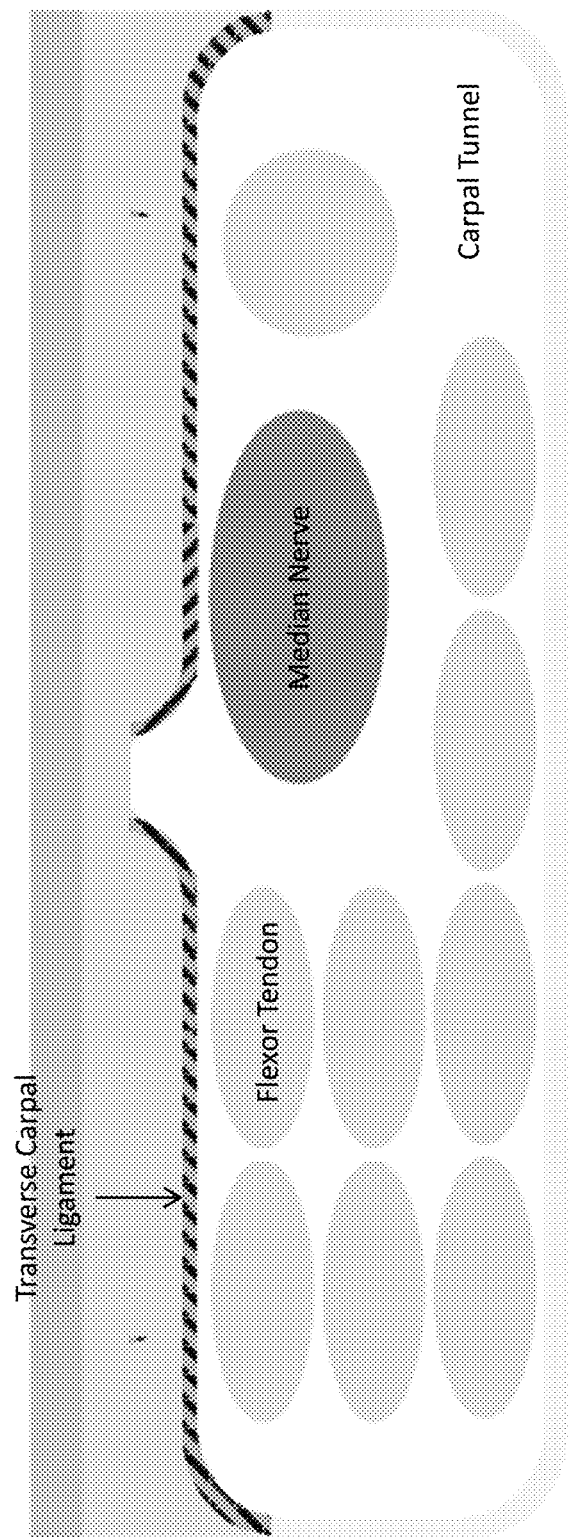

Referring now to FIG. 12E, cutting element 500 may be energized (or further pressure applied, in embodiments comprising mechanical cutting elements 510) to weaken the contacted portion of the transverse carpal ligament. Any of the described cutting elements 500 may be used for this application. The unipolar or bipolar electrocautery leads 520 may be particularly suitable for cutting the transverse carpal ligament, and bipolar embodiments may be preferred to protect the median nerve and its branches from injury. Once balloon 400 is inflated to a desired pressure, cutting elements 520 may be energized to weaken a contacted portion of the transverse carpal ligament such that it may be divided in combination with the tension applied by balloon 400, as shown in FIG. 12F.

In various embodiments, the position and orientation of cutting edge 500 may be rechecked throughout the inflation process. In one such embodiment, balloon 400 may be partially inflated to a first pressure suitable to give it some shape, at which point a recheck of position and orientation is performed before continuing. This may be repeated any number of suitable times during the inflation process to ensure that the transverse carpal tunnel is divided properly, and without causing damage to the median nerve and flexor tendons within the carpal tunnel.

Complete division of the transverse carpal ligament, in various embodiments, may be confirmed by inspection, lighting elements 700 (as previously described), an imaging modality, or some other suitable technique (e.g. measuring a corresponding reduction in balloon pressure associated with dividing the transverse carpal ligament and relieving the pressure within the carpal tunnel).

Referring now to FIG. 13, in an embodiment, a kit 1000 may be provided along with device 200 to facilitate introduction of the device 200 into the carpal tunnel. Kit 1000, in various embodiments, may include an imaging modality 1010, such as an ultrasound probe, a needle 1020, and a guidewire 1030. Kit 1000 may also include various dilators, guides or catheters, as well as disposables such as sheath for the ultrasound probe (not shown).

The method of using the device to divide the transverse carpal ligament can be consistent with the general method. Although the procedure may be guided by direct inspection, lighting elements 700 or other technique, ultrasound guidance may be particularly useful. Ultrasound of the wrist is a well-established technique which can clearly delineate the transverse carpal ligament and its association with the median nerve. It is routinely used to direct injections in the vicinity of the median nerve to relieve symptoms of carpal tunnel syndrome.

With reference now to FIGS. 14A-14I, there is provided a method of use of device 200 to treat carpal tunnel syndrome using ultrasound guidance. The forearm and hand (FIG. 14A) are sterilely prepped and draped with the hand in the hyperextended position. Local, regional or general anesthesia may be instituted. A tourniquet may be used but is not necessary. Anatomic landmarks are marked on the skin using palpation and ultrasound imaging of the wrist. The proximal and distal edges of the transverse carpal ligament can be identified as is the path of the palmaris longus tendon. The path of the median nerve is followed as it passes into and out of the carpal tunnel deep to the transverse carpal ligament. Any anatomic anomalies (e.g. bifid median nerve) or other pathology is identified. Measurements can be taken using ultrasound or other modalities including determining the width of the transverse carpal ligament. This allows the operator to select the appropriate size kit instruments and cutting balloon catheter.

A skin entry site can be identified in the distal forearm several centimeters proximal to the proximal edge of the transverse carpal ligament. The entry site is generally on the ulnar side of the parlmaris longus tendon and hence the median nerve providing a flat, straight trajectory to the proximal edge of the transverse carpal ligament. Of course, alternatively, the skin entry point may be in the hand with the device passing through the carpal tunnel from distal to proximal. The device may also be designed to penetrate the carpal tunnel from a medial or lateral direction with the balloon inflating along the long axis of the tunnel although this approach introduces several additional challenges such as maneuvering around the radial and ulnar arteries.

Figure 14A:
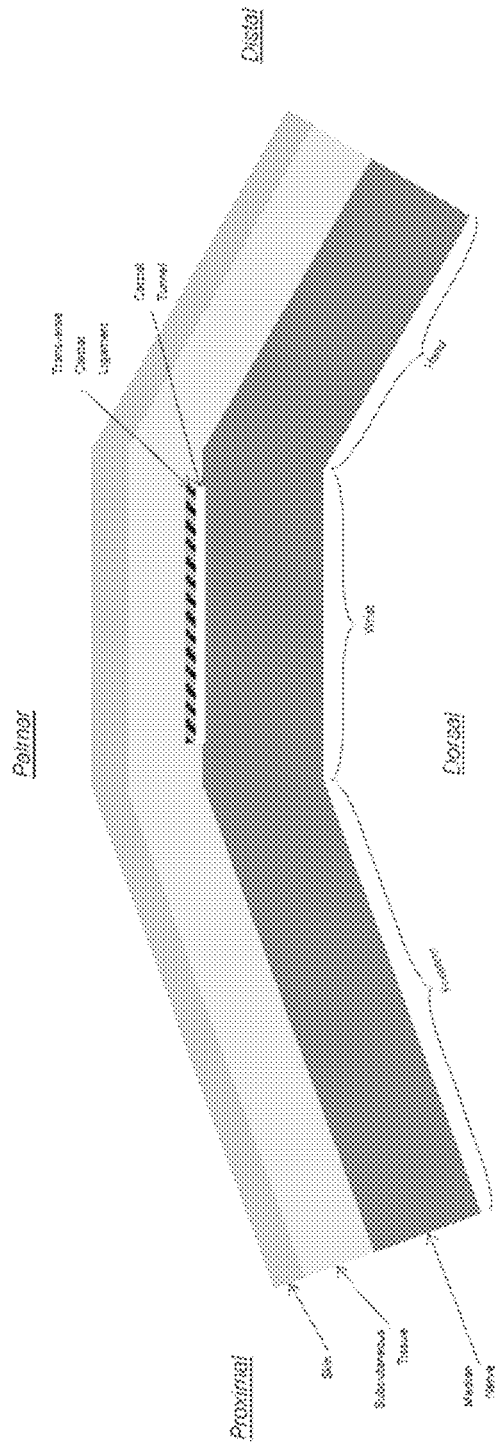
Figure 14B:
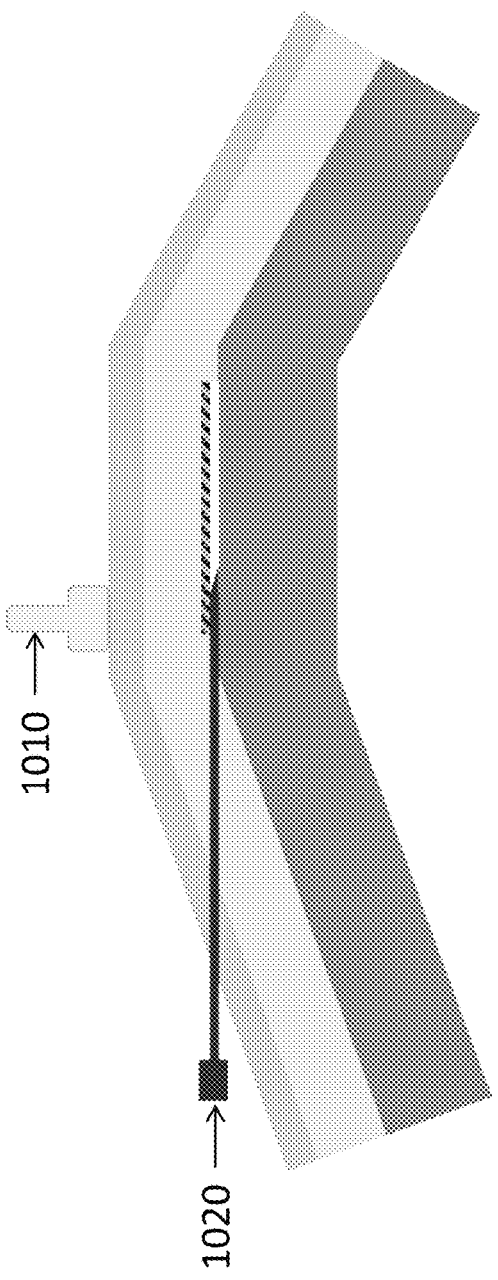

Needle 1020 is inserted, as shown in FIG. 14B, at the skin entry site and advanced from proximal to distal until it passes into the carpal tunnel just deep to the transverse carpal ligament. Ultrasound imaging can be used to confirm that the tip of needle 1020 enters the carpal tunnel in the correct location, on the ulnar side of median nerve. Needle 1020 can be used to inject fluid or local anesthetic into the carpal tunnel, if desired. This injection can be used to dissect tissues away from each other and create working space.

Figure 14C:
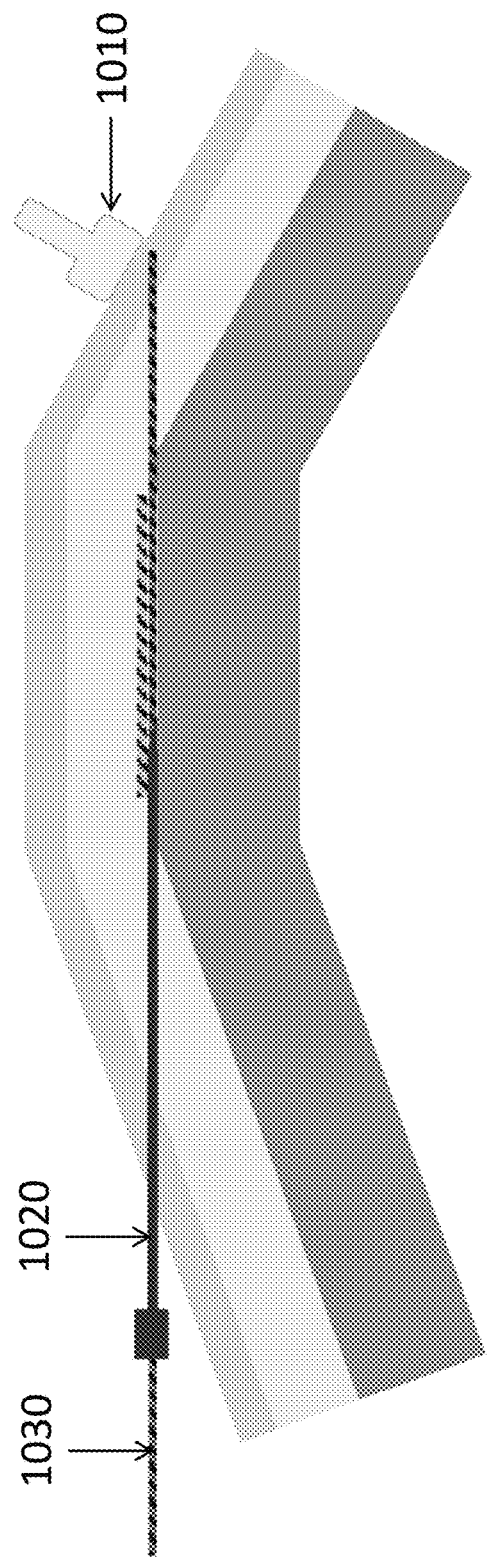
Figure 14D:
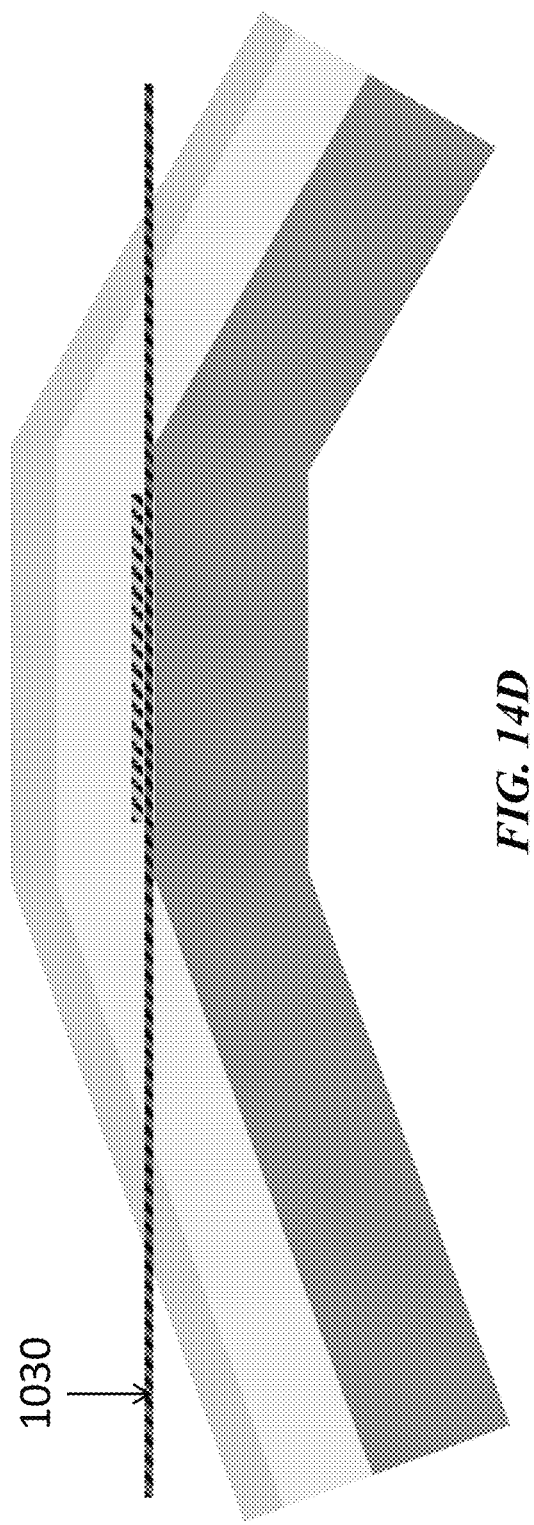

Guidewire 1030 is then inserted, as shown in FIG. 14C, into needle 1020 and advanced through the carpal tunnel along a trajectory that runs just deep to the transverse carpal tunnel and, again, ulnar to the median nerve. Guidewire 1030 generally has a straight tip and is stiff enough that it can penetrate through the tissues bluntly. The tip of guidewire 1030 can be tracked by ultrasound as it passes through the carpal tunnel and exits past the distal edge of the transverse carpal ligament. At a minimum guidewire 1030 should pass a few centimeters past this edge to provide an adequate rail for the balloon catheter. Ideally, guidewire 1030 will be advance further so that it exits through the skin of the palmar surface of the hand between the thenar and hypothenar eminences. This can be done under ultrasound guidance to assure that it exits cleanly and avoid critical hand structures such the arterial palmer arch. Once the tip of guidewire 1030 tents the skin of the hand, a small nick in the skin with a knife blade will allow it to exit. Alternatively, needle 1020 can be advanced over guidewire 1030 so that it penetrates the skin in the hand. Having a guidewire 1030 that exits the skin provides excellent column strength to facilitate positioning of device 200. Needle 1020 can thereafter be removed, as shown in FIG. 14D.

Figure 14E:
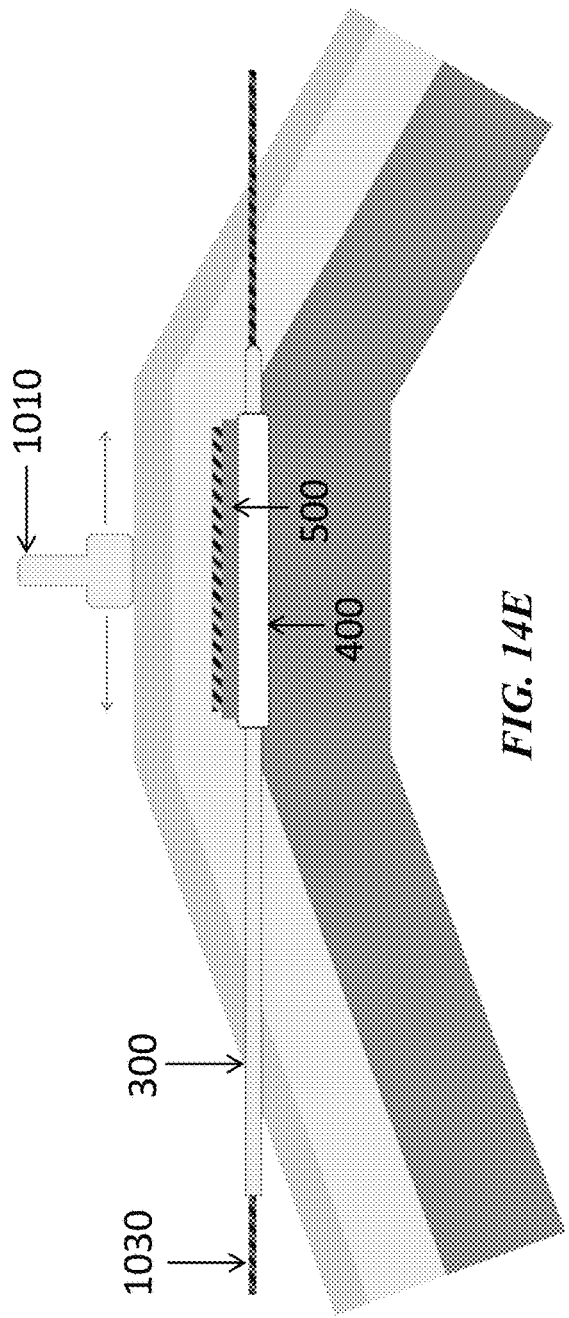

An appropriately sized device 200 is then selected and advanced over guidewire 1030 into the carpal tunnel, as shown in FIG. 14E. Device 200 can then be carefully positioned to ensure that its axial orientation is correct, with cutting element 500 positioned superficially, just under the transverse carpal ligament. Its longitudinal position can be adjusted so that cutting element 500 spans the entire width of the ligament. This positioning can be confirmed using ultrasound guidance. If the device contains lighting elements 700 previously described, these can be activated to confirm that cutting element 500 fully straddles the ligament.

Figure 14F:
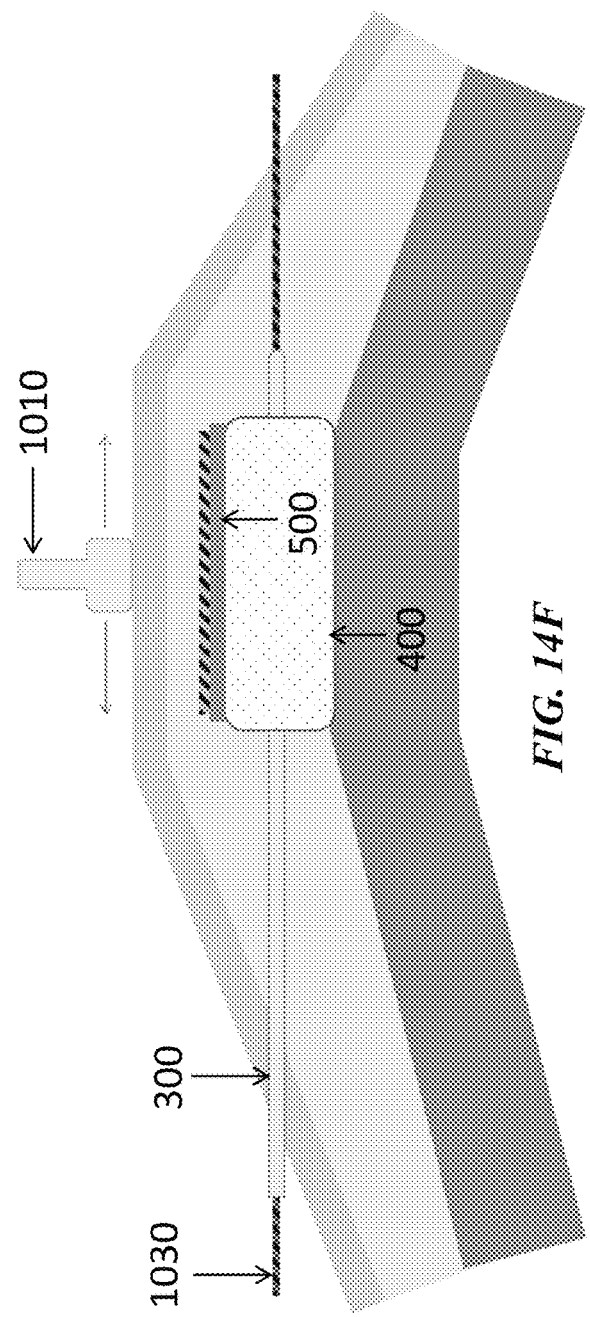

Once device 200 is properly positioned, balloon 400 may be inflated to a specified pressure with fluid, as shown in FIG. 14F. The fluid can be any liquid including saline or contrast material including echo contrast material or gas including air, carbon dioxide or oxygen. Balloon inflation can be monitored by direct inspection and palpation of the hand or by ultrasound guidance. The operator confirms that balloon 400 inflates uniformly while maintaining its axial orientation and dissecting the transverse carpal ligament from the deeper structures including the median nerve. If device 200 has the lighting element 700 functionality, this can be used to reconfirm balloon position. If the position is not optimal, balloon 400 can be deflated and the device 200 repositioned before reinflating.

If device 200 has sensing and/or stimulating functionality (e.g., elements 600), these can now be used to confirm that cutting element 500 is not positioned too close to the median nerve, its branches or other nerves. The elements 600 may be connected to a signal detector and/or stimulator, respectively, as shown back in FIGS. 7A-7C. If these leads 600 are on the same (superficial) surface of balloon 400 as cutting element 500, they are used to confirm the absence of nearby neuroelectrical activity. If they are located on the opposite (deep) surface of balloon 400, they are used to confirm that the median nerve is away from cutting element 500 by sensing its signal or stimulating it.

Figure 14G:
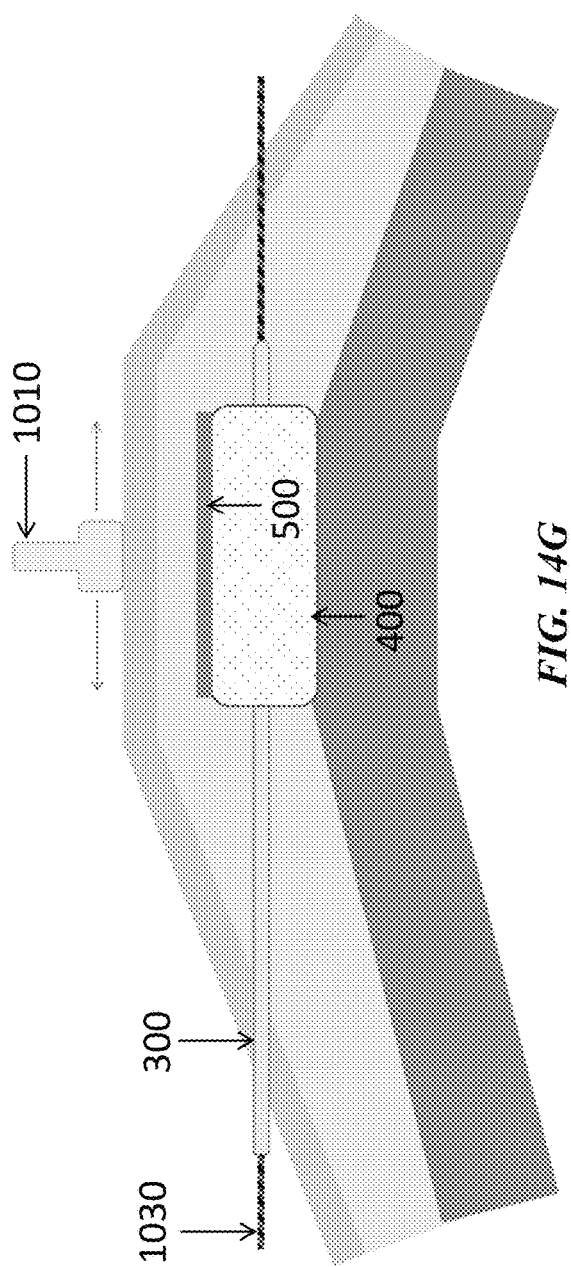

Once the position of cutting element 500 relative to the transverse carpal ligament and median nerve is confirmed, cutting element 500 is activated, as shown in FIG. 14G. If cutting element 500 is an electrocautery lead 520, it is connected to a radiofrequency generator. The generator is activated delivering radiofrequency energy to the lead 520 as it cuts through the ligament. The cutting process can be monitored by ultrasound and/or the lighting elements 700, if present.

Figure 14H:
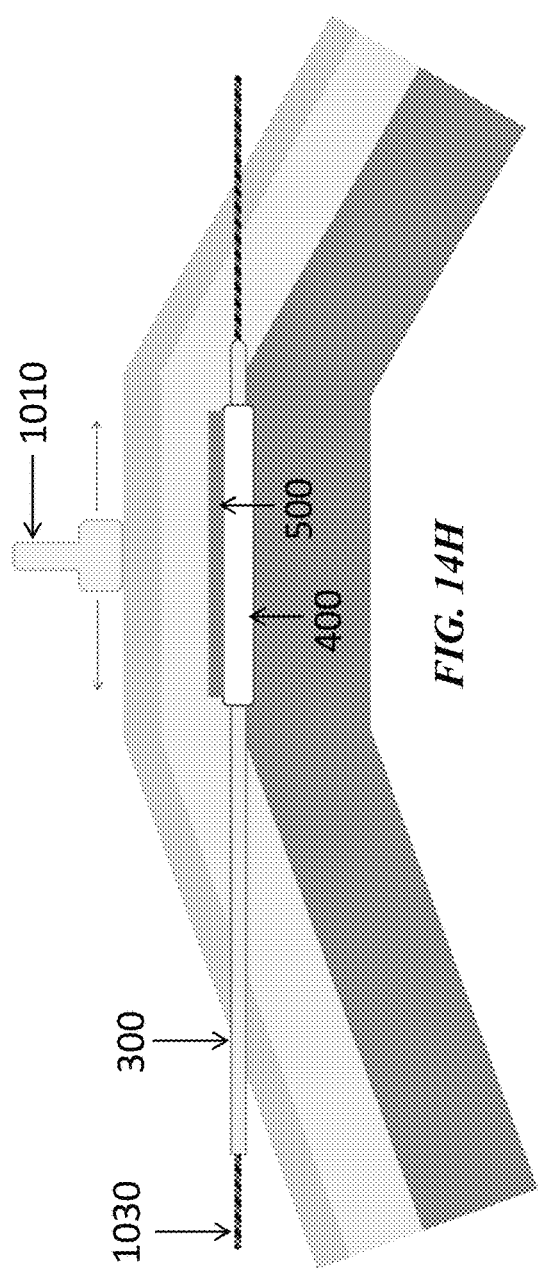
Figure 14I:

Once the cutting process is terminated, balloon 400 is deflated and the completeness of the division of the transverse carpal ligament is confirmed by ultrasound or other means, as shown in FIG. 14H. Device 200 and guidewire 1030 can be removed, as shown in FIG. 14I. Additional local anesthesia can be infiltrated into the wrist. Sterile dressings are applied. Appropriate post-operative care is instituted.

While the present disclosure has been described with reference to certain embodiments thereof, it should be understood by those skilled in the art that various changes may be made and equivalents may be substituted without departing from the true spirit and scope of the disclosure. In addition, many modifications may be made to adapt to a particular situation, indication, material and composition of matter, process step or steps, without departing from the spirit and scope of the present disclosure. All such modifications are intended to be within the scope of the claims appended hereto.

What is claimed is:

1. A method for dividing a fibrous structure, the method comprising:
    positioning, proximate the fibrous structure, an expandable member having:
    a cross-sectional shape that expands radially in a first direction more than it expands in a second direction to provide the expandable member with an elongated cross-sectional shape when inflated; and
    a cutting element situated on an outer surface of the expandable member at a location that expands in the second direction;
    expanding the expandable member outwards in the first direction to push the fibrous structure in opposing lateral directions and stretch the fibrous structure taut against the cutting element such that a portion of the fibrous structure contacts a discrete portion of the cutting element; and
    activating the cutting element to weaken or cut the fibrous structure.

2. A method for dividing a fibrous structure as set forth in claim 1, wherein the expandable member is a balloon.

3. A method for dividing a fibrous structure as set forth in claim 1, wherein the cutting element is a blade.

4. A method for dividing a fibrous structure as set forth in claim 3, wherein the step of activating the cutting element includes expanding the expandable member to press the blade against the fibrous structure.

5. A method for dividing a fibrous structure as set forth in claim 1, wherein the cutting element includes a unipolar lead or bipolar leads.

6. A method for dividing a fibrous structure as set forth in claim 1, wherein the cutting element is an electrocautery lead.

7. A method for dividing a fibrous structure as set forth in claim 6, wherein the step of activating the cutting element includes delivering radiofrequency energy to the electrocautery lead.

8. A method for dividing a fibrous structure as set forth in claim 1, wherein the step of expanding the expandable member further serves to manipulate a position of an anatomical structure located near the expandable member.

9. A method for dividing a fibrous structure as set forth in claim 1, further comprising the step of providing at least one element configured for sensing, stimulating, or both sensing and stimulating neuroelectrical activity.

10. A method for dividing a fibrous structure as set forth in claim 9, wherein the at least one element is situated on a surface of the expandable member.

11. A method for dividing a fibrous structure as set forth in claim 9, further comprising the step of determining whether a nerve is present in the vicinity of the at least one element, comprising at least one of:
    monitoring feedback from the at least one element for signals associated with neurological activity; and
    emitting, via the at least one element, a signal suitable for stimulating neuroelectrical activity.

12. A method for dividing a fibrous structure as set forth in claim 11, further comprising the step of adjusting a position, an orientation, or both a position and an orientation of the cutting element responsive to detecting the presence of a nerve in a vicinity of the sensing or stimulating element.

13. A method for dividing a fibrous structure as set forth in claim 9, wherein the at least one element is a sensing element or an element configured for both sensing and stimulating neuroelectrical activity.

14. A method for dividing a fibrous structure as set forth in claim 13, wherein the step of determining whether a nerve is present in the vicinity of the at least one element includes monitoring feedback, from the sensing element or element configured for both sensing and stimulating neuroelectrical activity, to detect an electrical signal emanating from the nerve at baseline, from activation of motor nerve fibers during normal muscle contraction, or during electrical stimulation of the nerve.

15. A method for dividing a fibrous structure as set forth in claim 9, wherein the at least one element is a stimulating element or an element configured for both sensing and stimulating neuroelectrical activity.

16. A method for dividing a fibrous structure as set forth in claim 15, wherein the step of determining whether a nerve is present in the vicinity of the at least one element includes emitting, from the stimulating element or element configured for both sensing and stimulating neuroelectrical activity, an electrical stimulus and motoring the body for a corresponding motor reaction.

17. A method for dividing a fibrous structure, the method comprising:
    positioning, proximate the fibrous structure, a device having:
    an expandable member having a cross-sectional shape that expands radially in a first direction more than it expands in a second direction to provide the expandable member with an elongated cross-sectional shape when inflated; and
    a cutting element situated on an outer surface of the expandable member at a location that expands in the second direction;
    expanding the expandable member in the first direction to stretch the fibrous structure to contact the cutting element;
    delivering an electrical stimulus to determine whether the expandable member along with the cutting element are appropriately positioned to cut the fibrous structure; and
    activating the cutting element to weaken or cut the fibrous structure.

* * * * *